United States Patent
Takagi et al.

(10) Patent No.: US 6,438,438 B1
(45) Date of Patent: Aug. 20, 2002

(54) METHOD AND SYSTEM FOR MANUFACTURING SEMICONDUCTOR DEVICES, AND METHOD AND SYSTEM FOR INSPECTING SEMICONDUCTOR DEVICES

(75) Inventors: Yuji Takagi, Yokohama; Hideaki Doi, Tokyo; Makoto Ono, Yokohama, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/002,529

(22) Filed: Jan. 2, 1998

Related U.S. Application Data

(63) Continuation of application No. 08/362,763, filed on Dec. 22, 1994, now Pat. No. 5,801,865.

(30) Foreign Application Priority Data

Dec. 28, 1993 (JP) .............................................. 5-334606

(51) Int. Cl.[7] .............................................. G06F 19/00
(52) U.S. Cl. ........................ 700/121; 700/110; 702/35; 356/237.5; 382/149
(58) Field of Search ................................ 700/121, 108, 700/109, 110; 702/182, 183, 184, 185, 35, 81–84; 356/237, 237.1, 237.2, 237.4, 237.5; 382/149, 144, 145

(56) References Cited

U.S. PATENT DOCUMENTS

| 4,253,768 A | 3/1981 | Karoshuk et al. ............ 356/431 |
| 4,587,617 A | 5/1986 | Barker et al. ................ 364/507 |
| 5,129,009 A | 7/1992 | Lebenu ........................... 382/8 |
| 5,210,041 A | 5/1993 | Kobayashi et al. ............. 437/8 |
| 5,219,765 A | 6/1993 | Kashida et al. ................ 437/8 |
| 5,240,866 A | 8/1993 | Friedman et al. .............. 437/8 |
| 5,301,248 A | 4/1994 | Takanori et al. ............... 382/8 |
| 5,325,445 A | 6/1994 | Herbert ........................ 382/38 |
| 5,426,506 A | 6/1995 | Ellingson et al. ........... 356/369 |
| 5,434,790 A | 7/1995 | Saka et al. ................... 364/468 |
| 5,440,649 A * | 8/1995 | Kiyasu et al. ............... 382/147 |
| 5,479,252 A * | 12/1995 | Worster et al. .............. 356/237 |
| 5,801,965 A * | 9/1998 | Takagi et al. ................ 364/552 |
| 5,923,430 A * | 7/1999 | Worster et al. .............. 356/394 |
| 5,982,921 A * | 11/1999 | Alumot et al. ............... 382/145 |
| 6,014,461 A * | 1/2000 | Hennessey et al. ......... 382/195 |
| 6,021,380 A * | 2/2000 | Fredriksen et al. ........... 702/35 |

FOREIGN PATENT DOCUMENTS

| JP | 54-101390 | 8/1979 |
| JP | 61-151410 | 10/1986 |
| JP | 62-43505 | 2/1987 |
| JP | 02-170279 | 7/1990 |
| JP | 04-72552 | 3/1992 |

OTHER PUBLICATIONS

Luria et al., "Automatic Defect Classification Using Fuzzy Logic", *ASMC*, 1993, Boston, MA (three pages).

* cited by examiner

Primary Examiner—Paul P. Gordon
(74) Attorney, Agent, or Firm—Mattingly, Stanger & Malur, P.C.

(57) ABSTRACT

The present invention relates to a method and system of inspecting a product, including extracting defects from the product, classifying the defects on the basis of information about the extracted defects representing the analogy of the defects, extracting the feature data of the defects on the basis of the result of defect classification, and feeding back the feature data of the extracted defects for inspection. The method and system is characterized in that the extracted feature data of the defects is fed back for inspecting the product. The present invention also relates to a method of manufacturing a semiconductor electric or electronic device, including extracting defects from the semiconductor electric or electronic device, classifying the defects on the basis of information about the extracted defects representing the analogy of the defects, extracting the feature data on the defects on the basis of the result of defect classification, and feeding back the feature data of the extracted defects to an apparatus for manufacturing the semiconductor electric or electronic device.

11 Claims, 23 Drawing Sheets

401: G-COMMON LINE
402: D-EVEN COMMON LINE
403: D-ODD COMMON LINE
404: SHORT CIRCUIT
407: TFT
408: TRANSPARENT PHOTOCATHODE
411 TO 415: G LINES
421 TO 425: DLINES

METHOD AND SYSTEM FOR MANUFACTURING SEMICONDUCTOR DEVICES, AND METHOD AND SYSTEM FOR INSPECTING SEMICONDUCTOR DEVICES

This application is a continuation application of U.S. Pat. No. 5,801,965 issued Sep. 1, 1998.

BACKGROUND OF THE INVENTION

The present invention relates to a method and system for efficiently manufacturing semiconductor electric or electronic devices or the like with high reliability and an inspection method and system for inspecting the semiconductor devices.

A conventional manufacturing process control system controls a manufacturing process on the basis of data obtained through the automatic inspection and repair of products. When the manufacturing process control system inspects products by an automatic inspecting system, the parameters of defect identifying standards to be used by the automatic inspection system are changed properly to enhance the reliability of inspection when the automatic inspection system provides excessively large amount of false information regarding nondefective products as defective or when residual defect ratio is excessively large.

A product inspected by the automatic inspection system and proved to be nondefective is sent to the next process, and repairable defective products are sent to a repairing process and are sent to the next process after being repaired. The operator monitors the condition of the manufacture of products statistically and, when necessary, changes the parameters for controlling the condition of the manufacturing machines to regulate the condition of the manufacturing process.

More concretely, in a semiconductor manufacturing process, presumably defective products found by using a visual inspection instrument, such as disclosed in Japanese Patent Laid-open (Kokai) No. 61-151410 or No. 62-43505, or a foreign matter inspection instrument, such as disclosed in Japanese Patent Laid-open (Kokai) No. 54-101390, for specifying presumably defective products are examined visually by means of a microscope included in the inspection instrument or a separate microscope to classify defects including foreign matters and defective patterns, and false information. A method of classifying detected defects using a multifocus image is disclosed in Japanese Patent Laid-open (Kokai) No. 2-170279.

Recently, Galai Laboratory of Israel and ADE Co. of the U.S.A. published cooperatively an automatic classification technique (M. Luria, E. Adin, M. Moran, D. Yaffe and J. Kawaski, "Automatic Defect Classification Using Fuzzy Logic", ASMC '93 Boston Mass., 1993), the details of which is unknown. Results of classification of defects are analyzed, manufacturing machines presumably causative of defects are specified on the basis of the results of analysis and results of inspection carried out in other processes. Skilled members of the staff of the manufacturing process relevant to the specified manufacturing machine adjust the parameters for controlling the manufacturing machine and correct the manufacturing machine on the basis of their experiences.

In a manufacturing process for manufacturing thin-film transistor wafer for liquid crystal displays, short circuit defects are detected by using a short circuit inspecting instrument, such as disclosed in Japanese Patent Laid-open (Kokai) No. 4-72552, the short circuit defects are confirmed visually, and the short circuit defects are classified by causes including particles, aluminum residues and through holes.

The foregoing prior art designed for the automation of inspection or the automation of inspection and repair for a system for controlling manufacturing processes on the basis of the results of automatic inspection and repair of products has the following problems. The prior art automatic inspection system consists of a detecting system for detecting defects in the product, and an information processing system for analyzing information provided by the detecting system to see whether or not the product has defects and to classify defects by category. Therefore, when the quality of the product varies according to the variation of the manufacturing process within an allowable range and the automatic inspection system decides that the product is defective, the automatic inspection system needs readjustment.

Since the detection system and the information processing system are the inherent components of the automatic inspection system as mentioned above, it is difficult to alter the detection system and the information processing system substantially. Accordingly, the sensitivity of the like of the detecting system or parameters for controlling the information processing system is changed for the readjustment of the automatic inspection system. In most cases, the readjustment of the automatic inspection system to adjust the inspection criteria of the automatic inspection system to inspecting standards used in the manufacturing process is carried out by a trial-and-error method at the site of manufacture, which takes much time to make the automatic inspection apparatus function normally. If the automatic inspection system is an in-line inspecting apparatus, the operation of the associated production line must be suspended during the adjustment of the automatic inspection system.

Another automatic inspection system inspects a product to see whether or not the product is defective and, if the product has a defect, provides only information about the position of the defect in the product. When this automatic inspection system is used, defects must be classified by the operator, and it is possible to examine the parameters of the automatic inspection system to see if the parameters are proper only after the classification and analysis of the defects by the operator. Therefore, the automatic inspection system not only needs much time before the same starts normally functioning, the inspection system has the possibility of inspecting products according to inappropriate inspecting standards while the defects are being classified and analyzed.

Accordingly, if the automatic inspection system is not adjusted properly, products are inspected and repaired erroneously.

In the prior art automatic inspection system, nothing is considered about means for making the operator make a decision about whether or not correction is necessary, i.e., whether or not the defects are classified correctly, to control a correcting operation and for feeding back information about the results of examination of the results of defect classification made by the automatic inspection system by the operator to the automatic inspection system.

Similarly, when defect detection information provided by the automatic inspection system in an imperfectly adjusted condition is used as means for adjusting the manufacturing machine for manufacturing the products, it is impossible to adjust the parameters for controlling the operating condition of the manufacturing machine for properly manufacturing the products. Since correcting information produced on the basis of the results of inspection provided by the automatic inspection system is fed back to the automatic inspection system, the complete readjustment of the automatic inspection system takes much time.

Furthermore, although accurate information about defects in products and information about the working condition of a manufacturing process are necessary for securing the stability of the manufacturing process, it requires much time to examine the correlation between the manufacture of defective products and the condition of the manufacturing process, because the accurate analysis of defects and the readjustment of the manufacturing process are carried out simultaneously when the products are inspected by the aforesaid prior art automatic inspection system.

Still further, since the prior art automatic inspection system does not attach the results of inspection and the bases of the results of inspection to the inspected product, it is impossible to find which manufacturing process is causative of the defect or the causal relationship between a defect detected at the final stage of manufacture and a defect detected at the middle stage of manufacture is unknown even if the defect is detected by inspection in the next process or by final inspection.

SUMMARY OF THE INVENTION

It is an object of the present invention to provide an adjusting means capable of properly and quickly adjusting inspecting standards on the basis of which an automatic inspection system functions, in cooperation with the operator to thereby provide a method of manufacturing a semiconductor device or the like, capable of enabling automatic inspection and automatic repair, a manufacturing system for carrying out the method, an inspection method, and an inspection system for carrying out the inspection method.

With the foregoing object in view, the present invention provides the following means.

(A) An inspection system in a first aspect of the present invention comprises: an automatic inspection unit for inspecting a product according to predetermined inspecting standards and extracting defects in the product; a defect classifying and feature extracting unit for receiving information about the extracted defects provided by the automatic inspection unit, classifying the defects by category, providing the results of classification of the defects and extracting the feature data of the defects on the basis of the results of classification; and a feature data converting unit for converting the feature data into corresponding inspecting standards for the automatic inspection unit and feeding back inspecting standards obtained by conversion to the automatic inspection unit.

(B) An inspection system in a second aspect of the present invention comprises: an automatic inspection unit for inspecting a product according to predetermined inspecting standards and extracting defects in the product; a defect classifying and feature extracting unit for receiving information about the extracted defects provided by the automatic inspection unit, classifying the defects by category, providing the. results of classification of the defects and extracting the feature data of the defects on the basis of the results of classification; and a feature-parameter conversion unit for converting the feature data into parameters for controlling the condition of the manufacturing machine manufacturing the product, and feeding back the parameters obtained by conversion to the manufacturing machine to adjust the manufacturing machine.

(C) The defect classifying and feature extracting unit stated in (A) or (B) is provided with a teaching means capable of teaching a correct result of defect classification when the result of defect classification provided by the defect classifying and feature extracting unit is incorrect.

(D) The inspecting system stated in (A) or (B) is provided with an information showing means capable of visually showing the result of defect classification provided by the defect classifying and feature extracting unit to the operator to enable the operator recognize the result of defect classification and information relating thereto, and to change the information or add new information to the information.

(E) The inspecting system includes an information storage means for storing the information mentioned in (D) and information about each defect.

(F) The inspection system is capable of extracting the feature data of defects from a plurality of pieces of the information mentioned in (D) and stored in the information storage means mentioned in (E) and information about the defects in the product corresponding to the information mentioned in (D), the feature data is given to the feature data converting unit mentioned in (A), and amends the inspecting standards to be used by the automatic inspection unit mentioned in (A).

(G) The inspection system is capable of extracting the feature data of defects from a plurality of pieces of the information mentioned in (D) stored in the information storage means mentioned in (E) and the information about the defects in the product, gives the feature data to the feature-parameter conversion unit mentioned in (B) and adjusts the manufacturing machine mentioned in (B).

(H) The inspection system is capable of adding information about the manufacturing process in a condition where the defects have just developed to the information mentioned in (D) stored in the information storage means mentioned in (E) and the information about the defects in the product corresponding to the information mentioned in (D), and holding and presenting the condition of the manufacturing process and historical information about the mode of development of defects in connection with each other.

(I) The inspection system includes a teaching means capable of showing the information about the defects and the related information including information about the category of an unknown defect when the defect classifying and feature extracting unit mentioned in (A) or (B) is unable to classify the results of classification of defects in the product into existing categories, and of enabling the operator to assign a new or an existing category, a name and the like to the defect of an unknown category.

(J) The information about the defect mentioned in (E), (F), (G), (H) and (I) is an image information about the defect and a region surrounding the defect.

(K) The product inspected by the automatic inspection unit (1) stated in (A) is sent to a product repair unit according to the result of defect classification provided by the defect classifying and feature extracting unit mentioned in (A) or (B), and the product is subjected to a predetermined repairing work.

(L) The product repairing operation of the product repair unit mentioned in (K) can be controlled by the operator, and the product repair unit is capable of teaching a correct result of defect classification when the result of defect classification provided by the defect classifying and feature extracting unit mentioned in (A) or (B) is incorrect and of feeding back the information about the correct result of defect classification to the defect classifying and feature extracting unit.

(M) Pattern information about an image of a detected defect is used as the attribute of the defect mentioned in (A) or (B).

(N) Signal information about the information about the detected defect is used as the attribute of the defect mentioned in (A) or (B).

(O) Information about either the result of inspection of the product or the result of measurement of the product, or both the result of inspection of the product and the result of measurement of the product is attached to the product.

(P) A manufacturing machine presumably causative of the defect is selected in view of the result of deflect classification provided by the defect classifying and feature extracting unit mentioned in (B) and the attribute of the defect, and the feature data of the defect extracted by the defect classifying and feature extracting unit mentioned in (B) is sent to the feature-parameter conversion unit mentioned in (B).

Naturally, the inspection system is independent of the foregoing automatic inspection unit. However, the automatic inspection unit may be a unit provided with a monitoring apparatus for monitoring the condition of a product, capable of inspection or monitoring and incorporated into a manufacturing machine.

The operation of the foregoing means to achieve the object of the invention will be explained hereinafter with reference to FIG. 1.

A thick line 12 represents the flow of a product in a manufacturing process. An automatic inspection unit 1 inspects a product and extracts defects according to predetermined inspecting standards. A defect classifying and feature extracting unit 2 classifies defects and extracts the feature data of the defects.

The automatic inspection unit 1 gives defect information about the defects detected through inspection to the defect classifying and feature extracting unit 2. The defect information includes images of the defects, electric signals generated upon the detection, information on the basis of which the defects are identified, and the like. The defect classifying and feature extracting unit 2 classifies the defects on the basis of the the defect information. The defects are classified on the basis of various feature data on a rule basis or a model basis. A defect classification indicating unit 6 indicates the result of defect classification to enable the correction of the result of defect classification.

The defect classification indicating unit 6 shows the result of defect classification visually to enable an operator to recognize information including the result of defect classification and the related information and to change the information or add new information thereto.

The defect classifying and feature extracting unit 2 changes the interpretation of the feature data of the corresponding defect on the basis of the result of defect classification taught thereto by the defect classification indicating unit 6.

A feature data converting unit 3 is capable of converting the feature data of the defects classified by the defect classifying and feature extracting unit 2 into inspecting standards. The feature data converting unit 3 sends the inspecting standard obtained by converting the feature data to the automatic inspection unit 1. If the result of defect classification provided by the defect classifying and feature extracting unit 2 and the result of a decision made by the automatic inspection unit 1 are different from each other, the result of defect classification provided by the defect classifying and feature extracting unit 2 is reflected through the feature data converting unit 3 on the automatic inspection unit 1.

A feature-parameter conversion unit 4 is capable of converting the feature data of the defects classified by the defect classifying and feature extracting unit 2 into control parameters relating to manufacturing conditions for a product manufacturing machine 8 for manufacturing the product. The feature-parameter conversion unit 4 gives the control parameters obtained by converting the feature data to the product manufacturing machine 8. The defect classifying and feature extracting unit 2 is capable of selecting the product manufacturing machines 8 to be readjusted on the basis of the result of defect classification and of sending information to the feature-parameter conversion units 4 connected to the selected product manufacturing machines 8.

An information storage unit 7 connected to the defect classifying and feature extracting unit 2 stores all or part of defect information about each of the defects in the product received from the automatic inspection unit 1, the result of defect classification received from the defect classifying and feature extracting unit 2, information used for defect classification, and, when the defect classifying and feature extracting unit 2 is provided with a means for obtaining image information or electric signals, image information or electric signals about defects in the product, regions surrounding the defects or other portions characterizing the defects, which are different from the information obtained by the automatic inspection unit 1.

The defect classifying and feature extracting unit 2 is capable of receiving information about the operating condition of the product manufacturing machines 8. The information received by the defect classifying and feature extracting unit 2 is stored in addition to the information about the product in the information storage unit 7. The information about the defects and the like stored in the information storage unit 7 is subjected to statistical data processing when necessary and the statistically processed information is shown to the operator by the defect classification indicating unit 6 connected to the defect classifying and feature extracting unit 2. All or part of the information about each of the defects stored in the information storage unit 7 and the information provided by the defect classifying and feature extracting unit 2 are sent to a process control system 5.

A product sorting unit 9 selects defective products which are to be repaired and delivers the selected defective products onto a repair line 13 to send the defective products to relevant repair units 11 according to instructions given thereto from the defect classifying and feature extracting unit 2.

The repair units 11 may be substituted by a single repair unit capable of removing all kinds of defects or each of the repair units 11 may be capable of removing a specific defect. Although the repair units 11 are capable of automatic repairing operation, they enable the operator to determine whether or not repair is necessary, and, when the category of the defect is different from that determined by the defect classifying and feature extracting unit 2, they are capable of informing the defect classifying and feature extracting unit 2 to that effect.

An information attaching unit 14 attaches information about the result of inspection of the product by the automatic inspection unit 1 and the associated information to the product.

With the inspection system thus constructed efficient inspection of products is made possible for manufacturing products with high reliability according to the manufacturing process.

The present invention has the following advantages.

(A) Since the inspecting standards by which the automatic inspection unit inspects products can be automatically readjusted by the defect classifying and feature extracting unit 2 of FIG. 1 or can be semiautomatically readjusted through the feature data converting unit 3 of FIG. 1 under operator's supervision using the defect classification indicating unit 6 connected to the defect classifying and feature extracting unit 2, the inspecting standards can be readjusted to inspecting standards conforming to the process conditions without stopping the automatic inspection unit.

(B) Since the inspecting standards can be automatically readjusted by the defect classifying and feature extracting unit 2 of FIG. 1 or can be semiautomatically readjusted through the feature data comparing unit 3 of FIG. 1 under operator's supervision using the defect classification indicating unit 6 connected to the defect classifying and feature extracting unit 2, the inspecting reliability of the automatic inspection unit can be improved quickly.

(C) The effect mentioned in (A) curtails the time necessary for starting up the automatic inspection unit when products of one kind being inspected are changed for those of another kind.

(D) Since the effect mentioned in (A) curtails the time necessary for adjusting the automatic inspection unit, the number of products which are inspected on the basis of inappropriate inspecting standards can be reduced.

(E) Since the classification of defects by the defect classifying and feature extracting unit 2 of FIG. 1 enables the categories of defects to be known and thereby the manufacturing machines presumably causative of the defects can be determined. The manufacturing process can be stabilized quickly by adjusting the manufacturing machines taking into consideration the characteristic defects of the manufacturing machines through the operation of the feature-parameter conversion unit 4 of FIG. 1.

(F) The effect mentioned in (B) enables correct instructions to be given to the repairing process, so that the incorrect repair of products can be prevented.

(G) The defect classifying and feature extracting unit 2 of FIG. 1 is adjusted while defects are removed by operating a defect classification input unit 10 connected to the repair unit 11 of FIG. 1 and, consequently, the inspecting standards by which the automatic inspection unit inspects products can be readjusted.

(H) The defect classification indicating unit 6 processes the information stored in the information storage unit 7 of FIG. 1 and indicates the processed information to enable the operator to grasp easily the relation between the causes of defects and the condition of the manufacturing process.

(I) Information given to the information storage unit 7 of FIG. 1 is transferred to the process control system 5 of FIG. 1 to enable the control of the condition of the entire manufacturing process.

(J) When the result of defect classification provided by the defect classifying and feature extracting units 2 of the automatic inspection units installed respectively at different positions in the manufacturing process and the feature data of defects are compared and when the result of defect classification provided by the defect classifying and feature extracting units 2 are similar to each other, a portion of the manufacturing process between the automatic inspection units connected to those defect classifying and feature extracting units 2 need not be monitored and hence either of the upstream and downstream automatic inspection units of the manufacturing process may be omitted. The automatic inspection units can thus be installed at optimum positions in the manufacturing process.

(K) Since the information attaching unit 14 of FIG. 1 attaches the result of inspection and the associated information to the inspected product, the manufacturing processes causative of the defects and the causal relation between defects detected by inspection at the final stage and those detected at the middle stage can be known by comparing the information attached to the product and the result of inspection in the following manufacturing processes or the result of final inspection.

DESCRIPTION OF THE PREFERRED EMBODIMENTS

Figure 1:
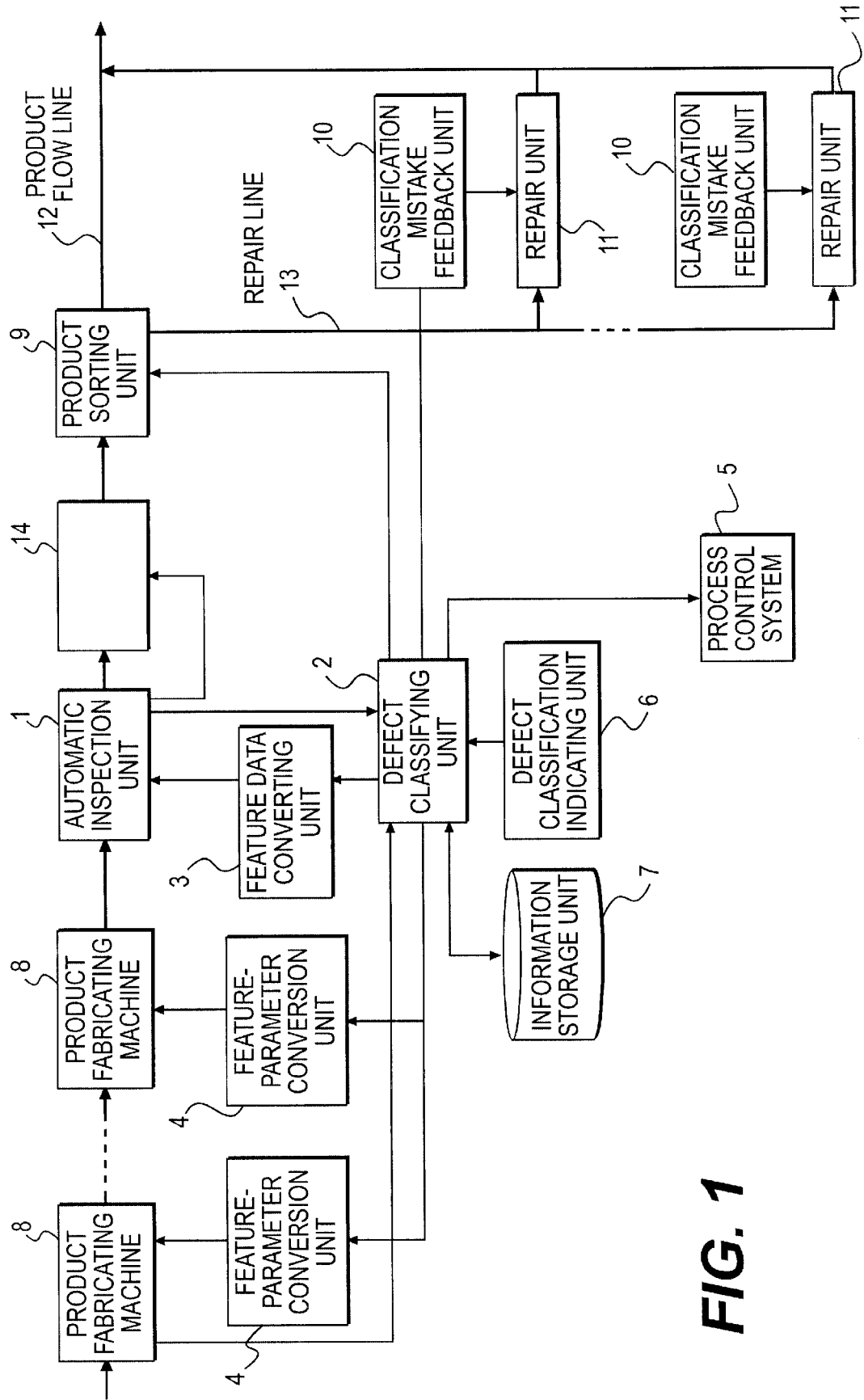
FIG. 1 is a block diagram for the concept of the present invention.

First, the conceptual intention of the present invention will be described with reference to FIG. 1 prior to the description of the preferred embodiments of the present invention.

A thick line 12 represents the flow of a product in a manufacturing process. An automatic inspection unit 1 inspects a product and extracts defects according to predetermined inspecting standards. A defect classifying and feature extracting unit 2 classifies defects and extracts the feature data of the defects. The automatic inspection unit 1 gives defect information about the defects detected through inspection to the defect classifying and feature extracting unit 2. The defect information includes images of the defects, electric signals generated upon the detection of the defects, information on the basis of which the defects are identified, and the like.

The defect classifying and feature extracting unit 2 classifies the defects on the basis of the defect information. The defects are classified on the basis of various feature data on a rule basis or a model basis. A defect classification indicating unit 6 indicates the result of defect classification to enable the correction of the result of defect classification. The defect classification indicating unit 6 shows the result of defect classification visually to enable the operator to recognize information including the result of defect classification and the related information and to change the information or add new information to the information. The defect classifying and feature extracting unit 2 changes the interpretation of the feature data of the corresponding defects on the basis of the result of defect classification taught thereto by the defect classification indicating unit 6.

A feature data converging unit 3 is capable of converting the feature data of the defects classified by the defect classifying and feature extracting unit 2 into inspecting standards. The feature data converting unit 3 sends the inspecting standards obtained by converting the feature data to the automatic inspection unit 1. If the result of defect classification provided by the defect classifying and extracting unit 2 and the result of a decision made by the automatic inspection unit 1 are different from each other, the result of defect classification provided by the defect classifying and feature extracting unit 2 is reflected through the feature data converting unit 3 on the automatic inspection unit 1.

A feature-parameter conversion unit 4 is capable of converting the feature data of the defects classified by the defect classifying and feature extracting unit 2 into control parameters relating to manufacturing conditions for a product manufacturing machine 8. The feature-parameter conversion unit 4 gives control parameters obtained by converting the feature data to the product manufacturing machine 8. The defect classifying and feature extracting unit 2 is capable of selecting the product manufacturing machine 8 to be readjusted on the basis of the result of defect classification and of sending information to the feature-parameter conversion unit 4 connected to the selected product manufacturing machine 8.

An information storage unit 7 connected to the defect classifying and feature extracting unit 2 stores all or part of defect information about each of the defects in the product received from the automatic inspection unit 1, the result of defect classification received from the defect classifying and feature extracting unit 2, information used for defect classification, and, when the defect classifying and feature extracting unit 2 is provided with a means for obtaining image information or electric signals, image information or electric signals about defects in the products, regions surrounding the defects or other portions characterizing the defects, which are different from the information obtained by the automatic inspection unit 1.

The defect classifying and feature extracting unit 2 is capable of receiving information about the operating condition of the product manufacturing machine 8. The information received by the defect classifying and feature extracting unit 2 is stored in addition to the information about the product in the information storage unit 7. The information about the defects and the like stored in the information storage unit is subjected to statistical data processing when necessary and the statistically processed information is shown to the operator by the defect classification indicating unit 6 connected to the defect classifying and feature extracting unit 2. All or part of the information about each of the defects stored in the information storage unit 7 and the information provided by the defect classifying and feature extracting unit 2 are sent to a process control system 335 of FIG. 2.

A product sorting unit 9 selects defective products which are to be repaired and delivers the selected defective products onto a repair line 13 to send the defective products to relevant repair units 11 according to instructions given thereto from the defect classifying and feature extracting unit 2.

The repair units 11 may be substituted by a single repair unit capable of removing all kinds of defects or each of the repair units 11 may be capable of repairing a specific defect. Although the repair units 11 are capable of automatic repairing operation, they enable the operator to determine whether or not repair is necessary, and, when the category of the defect is different from that determined by the defect classifying and feature extracting unit 2, they are capable of informing the defect classifying and feature extracting unit 2 to that effect.

An information attaching unit 14 attaches information about the result of inspection of the product by the automatic inspection unit 1 and the associated information to the product.

Figure 2:
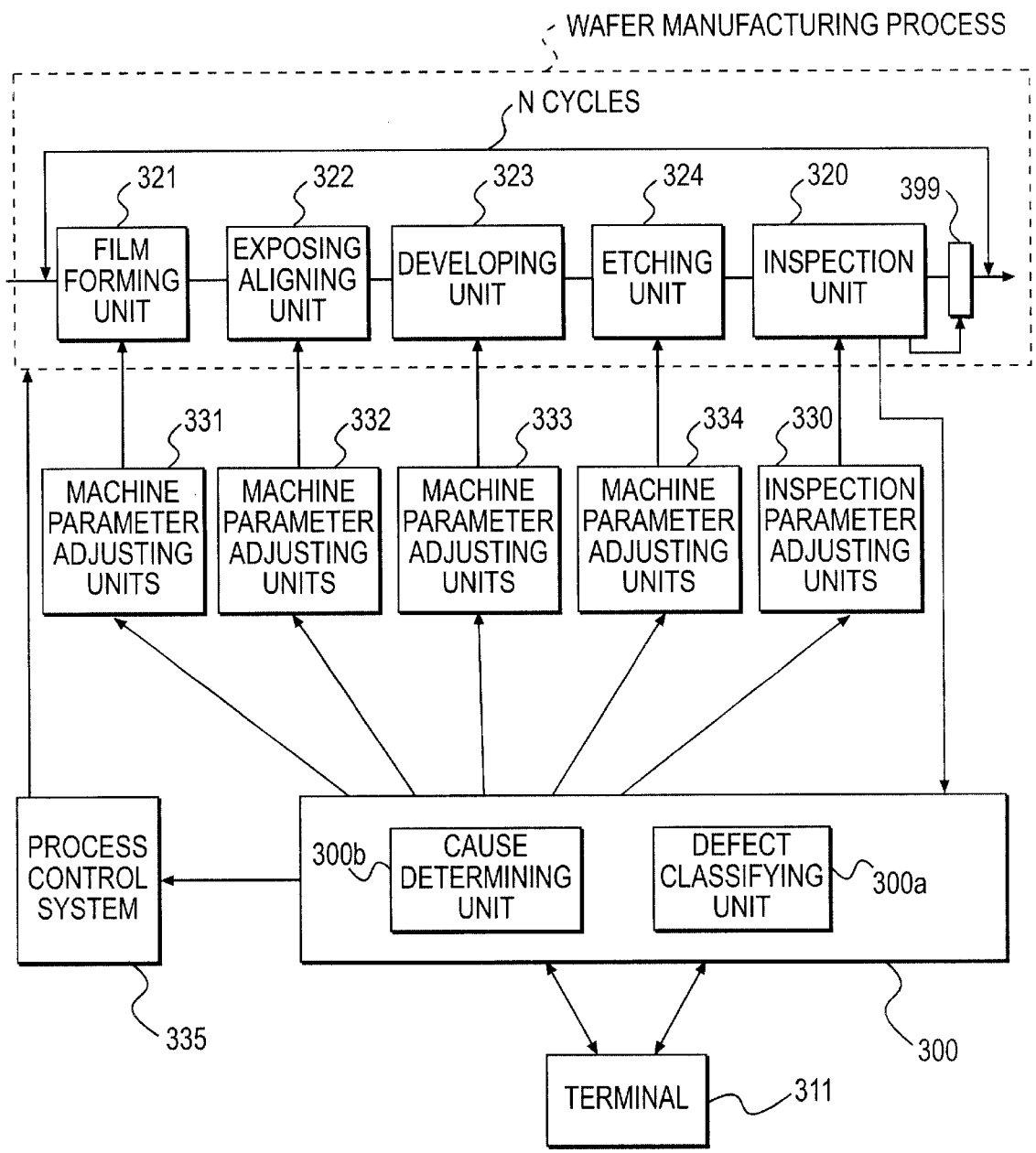
FIG. 2 is a block diagram of a semiconductor device manufacturing process incorporating the present invention.

FIG. 2 shows an inspection system in a first embodiment according to the present invention as applied to a semiconductor wafer manufacturing process. Briefly, the semiconductor wafer manufacturing process comprises a series of steps of forming a film on a wafer by a film forming unit 321, exposing the film to light in a pattern by an exposure unit 322, developing the film in the pattern by a developing unit 323, etching by an etching unit 324, and the series of steps is repeated a plurality of times to form stacked layers in patterns on the wafer.

While a plurality of cycles of the semiconductor wafer manufacturing process are repeated, an inspection unit 320 inspects products by a sampling inspection method or a total inspection method to determine the positions of presumed defects for quality control, and sends position information representing the positions of the presumed defects, detected image information, defect distribution information and the data of the wafer to a defect classifying and feature extracting unit 300 for classifying defects and extracting feature data of defects. A defect classifying and feature extracting unit 300a compares the information about each presumed defect with a defect model and a defect image data base for similarity examination to remove false information, and then classifies the defects. A cause determining unit 300b determines causes of the defects on the basis of information about the classified defects, time series information about distribution obtained and stored in the past, and the positional distribution of defects.

Figure 3:
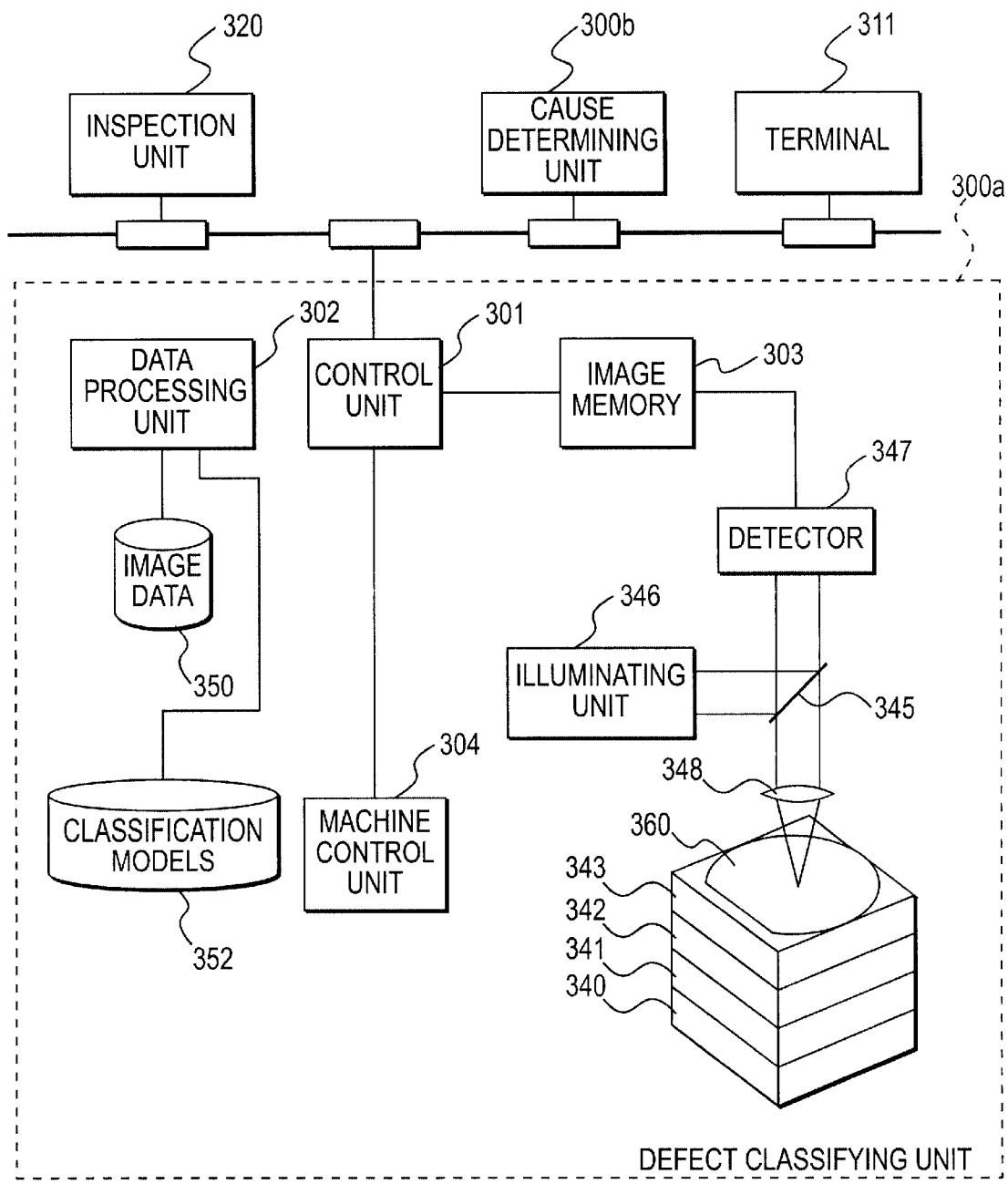
FIG. 3 is a block diagram of a defect classifying and feature extracting unit for classifying defects and extracting the feature data of defects.

FIG. 3 shows the configuration of the defect classifying and feature extracting unit 300 of FIG. 2. The defect classifying and feature extracting unit 300 is included in a network including the inspection unit 320, the cause determining unit 300b, and a terminal equipment 311 for indicating information to the operator, providing instructions and entering information by the operator, and is capable of communicating image information, defect information, process information and the like optionally.

The terminal equipment 11 is provided with a bit-mapped display to display image information. The terminal equipment 311 may be substituted by a character terminal equipment and a TV monitor. The defect classifying and feature extracting unit 300 comprises a control unit 301, a data processing unit 302, an image memory 303, a machine control unit 304 for controlling stages, a detector 347, an illuminating unit 341 for illuminating a wafer 360, a half mirror 345, a lens 348, an X-stage 340, a Y-stage 341, a θ-stage 342, a Z-stage 343, an image data storage unit 350, and a classification model storage unit 352 for storing classification models of shapes of defects, sizes of defects, colors of defects, positions of defects on wiring patterns, and textures of defects. The functions of these components may be substituted by those of the inspection unit 320. The components of the network may be electrically interconnected by a serial serial transmission system, such as RS232C, or a parallel transmission system, such as Centronics.

Figure 4:
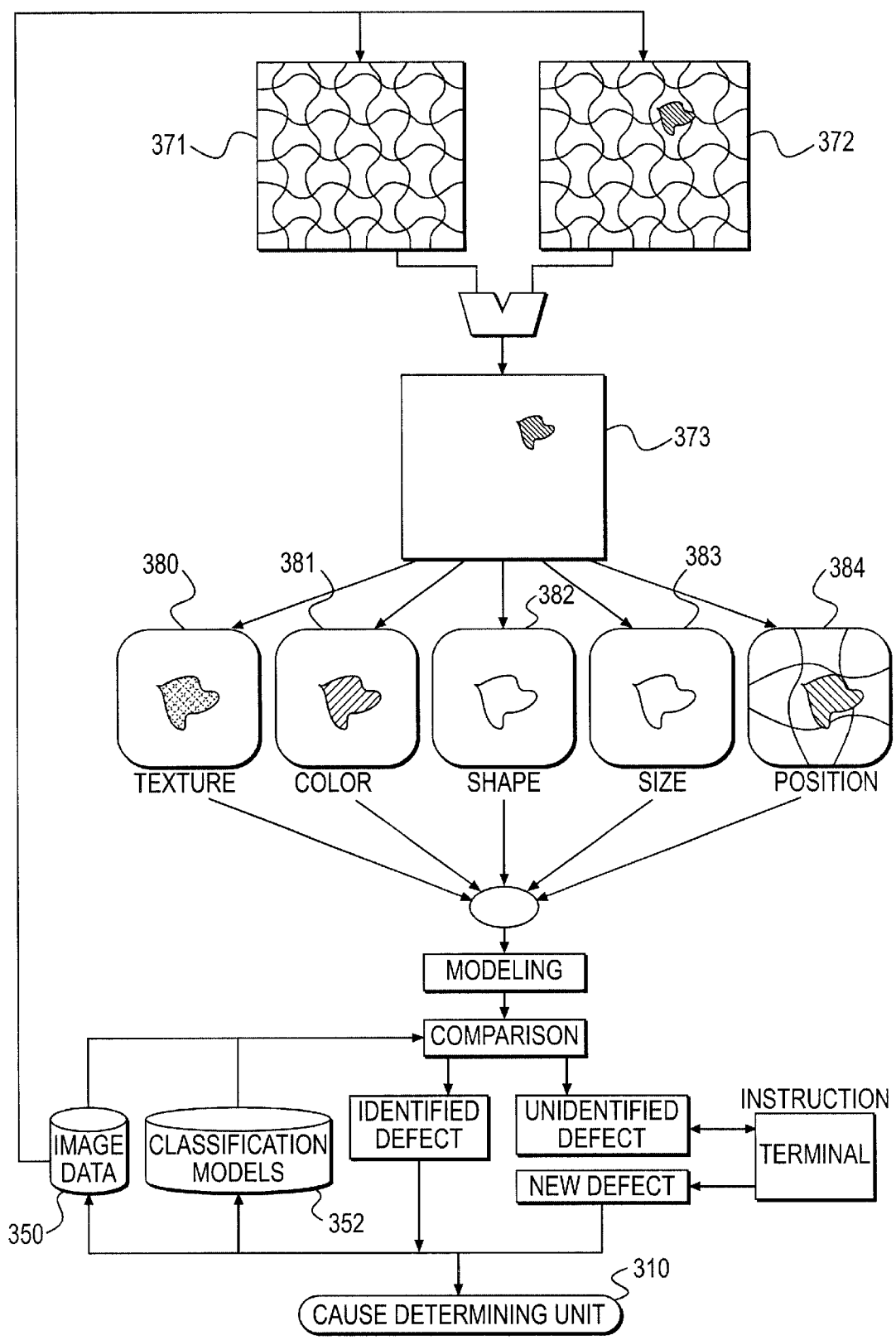
FIG. 4 is a conceptual block diagram for explaining a defect classifying method.

A defect classifying method to be carried out by the defect classifying and feature extracting unit 300 will be described hereinafter with reference to FIG. 4. When the inspection unit 320 finds a defect on the wafer, the detector 347 picks up an image 372 of the defect. The image is aligned with an image 371 of a nondefective portion of the wafer having the same pattern, i.e., a reference image, the difference between the image and the reference image is determined by a method, such as a method published in Denshi Joho Tsushin Gakkai Ronbunshi (Journal of Electronic Information Communication Society) D-II, Vol. J72-D-II, No. 12, pp. 2041–2050, the pattern is removed from the image and only the image of the defect is extracted to produce a defect image 373.

Feature data are extracted from information including texture information 380, color or density distribution information 381, shape information 382 obtained by detecting the outline information 3-D information obtained by varying focus, area information 383, and position information 384 about the position of the defect relative to the nearby wiring pattern provided by the inspection unit 320, and extracted from the defect image 373, and the detected defect is mapped in an n-dimensional feature data space consisting of several-n feature data.

Figure 5:
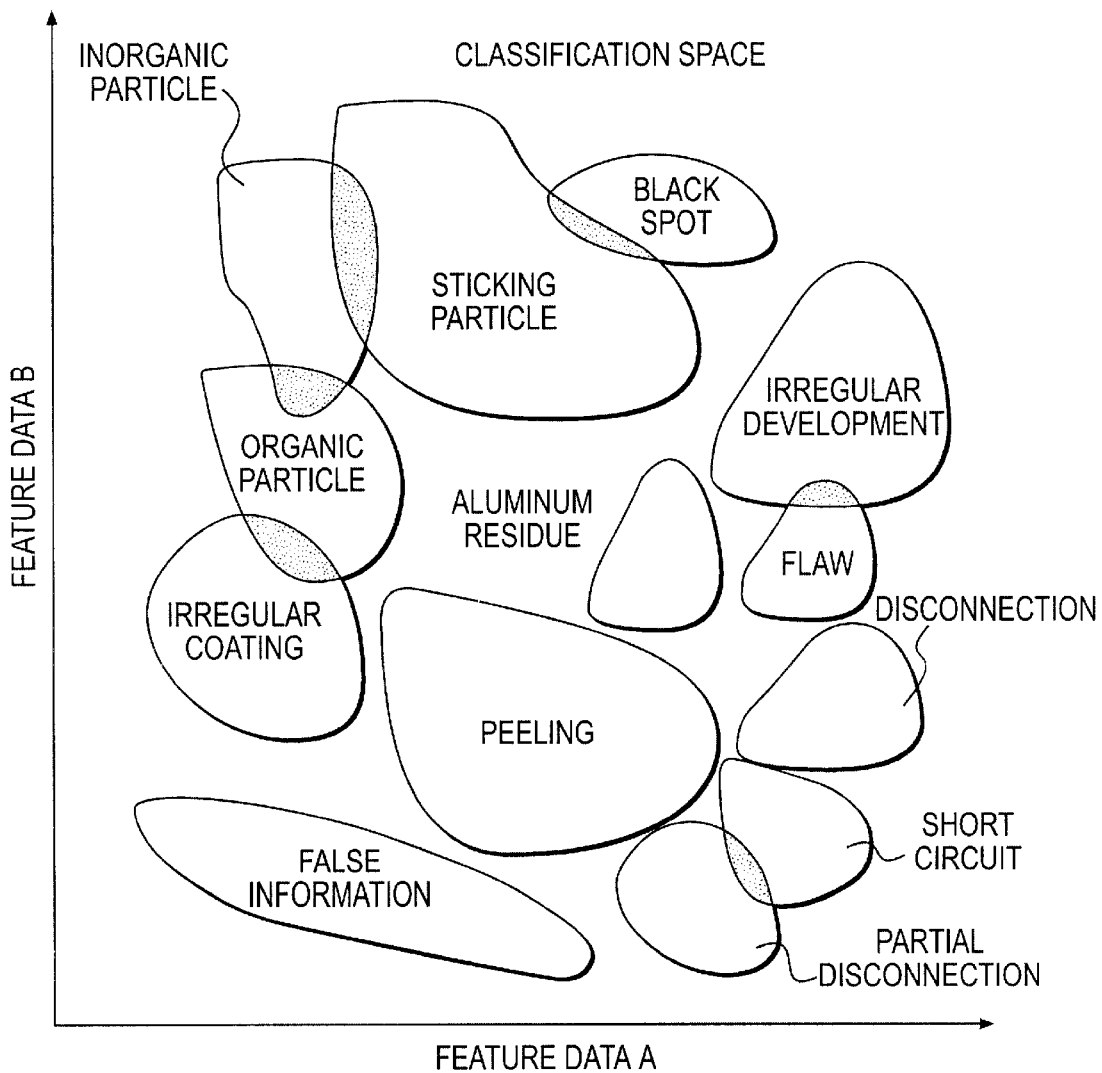
FIG. 5 is a diagrammatic view showing the distribution of defect clusters.

Classification models stored in the classification model storage unit 352 define regions corresponding to the feature data of defects in the n-dimensional space. The detected defect mapped in the n-dimensional feature data space is compared with the classification model, false information is removed, and then the defect is classified. When classifying the defect, the defect is identified by clusters defined in a classification space defined by feature data as shown in FIG. 5. Although FIG. 5 shows a two-dimensional space, practically, the classification space is an n-dimensional space, and the clusters of defects are defined by regions in the multidimensional space.

Figure 6:
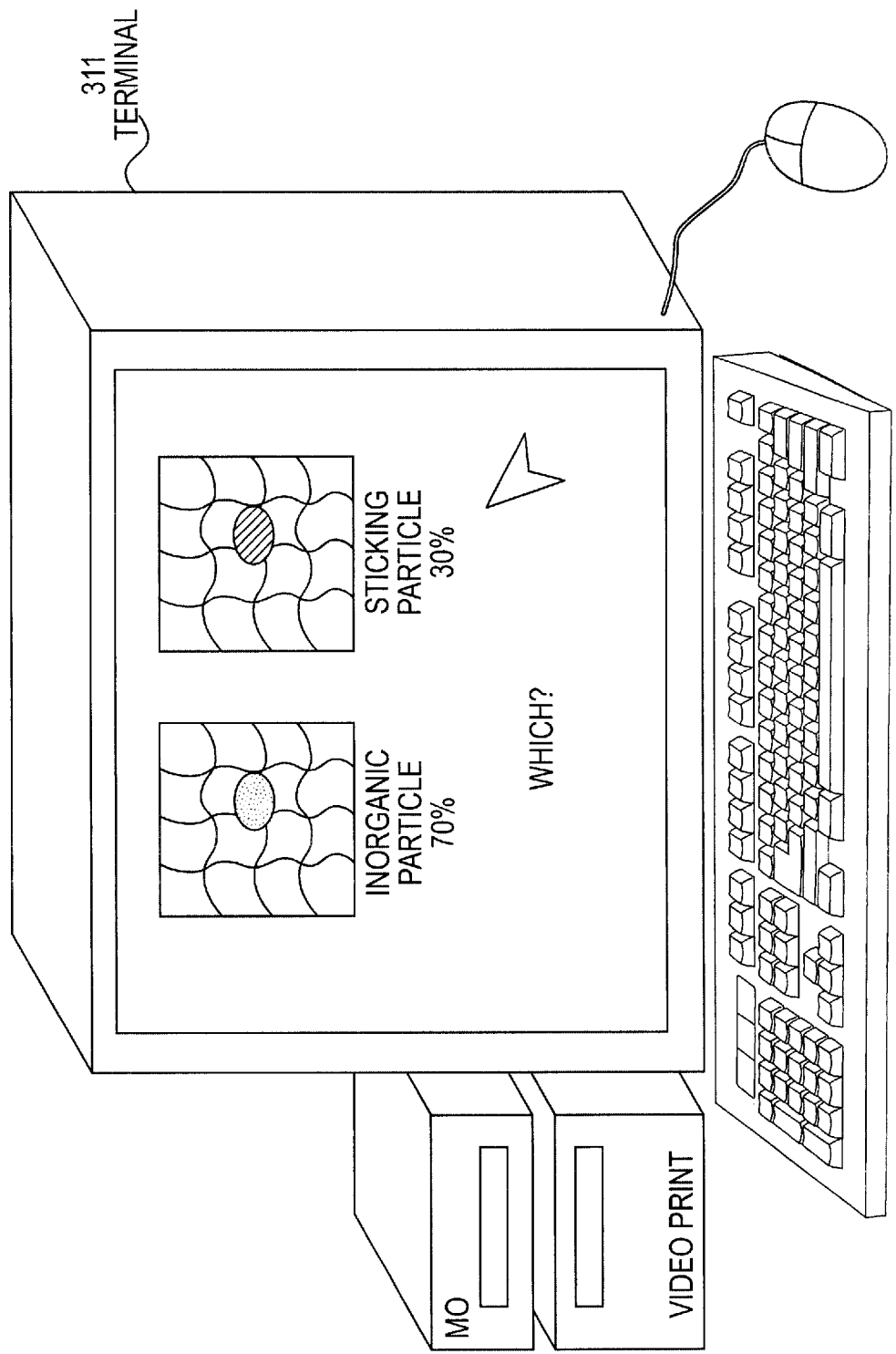
FIG. 6 is a perspective view of a terminal equipment, showing information displayed on a screen.
Figure 7:
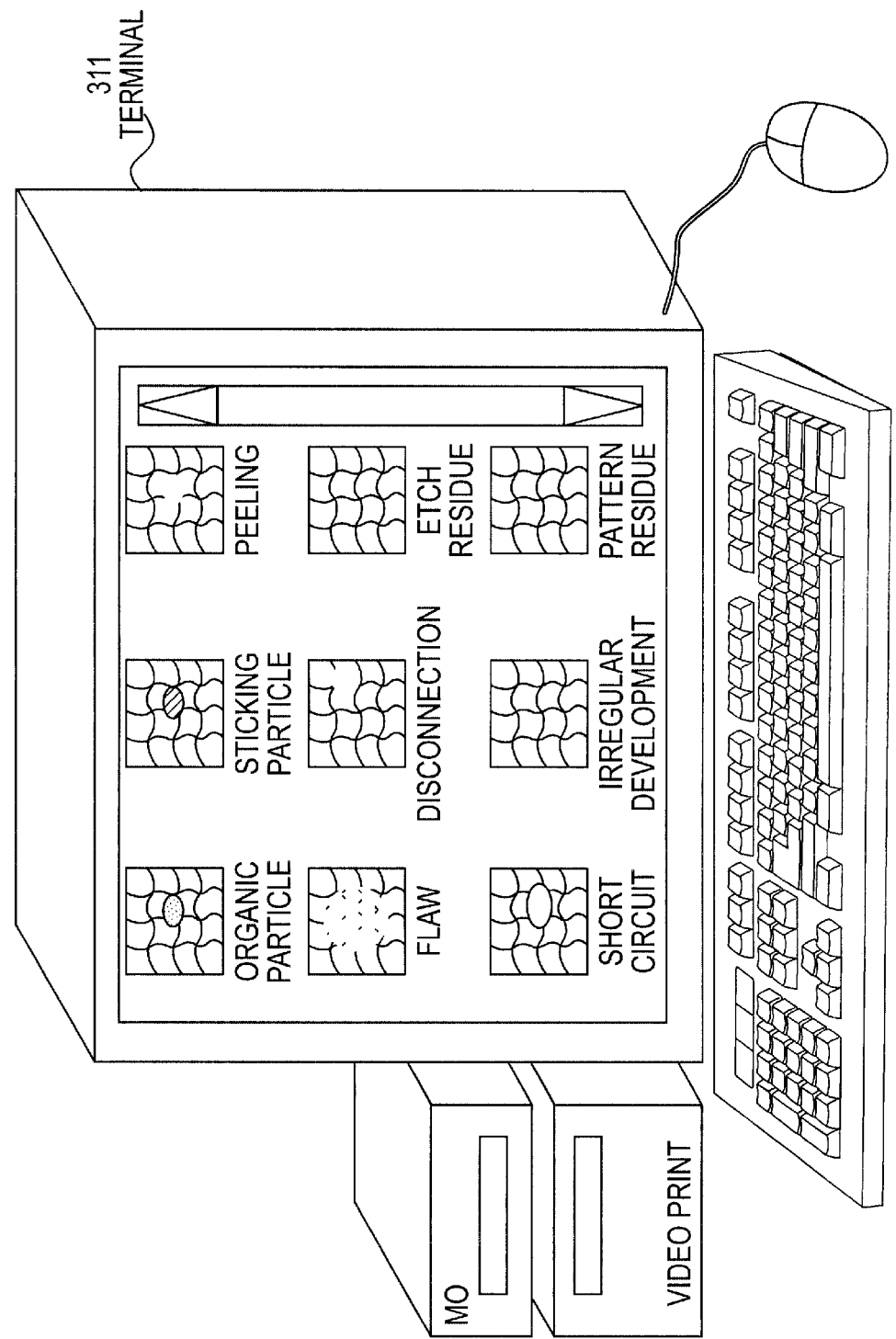
FIG. 7 is a perspective view of a terminal equipment, showing information displayed on a screen.

In FIG. 5, the category of a defect in an overlapping portion, namely, shaded region, of the clusters cannot be identified by a single category, typical defects included respectively in the overlapping clusters are displayed as shown in FIG. 6 to request the operator to specify the category of the defect. If the defect does not belong to any one of the clusters, representative defects are displayed in the increasing order of distance from the classification space as shown in FIG. 7. When one of the displayed defects is specified, an additional cluster is registered. Even if the category of the defect could be identified, the cluster can be changed or renewed by the operator.

Detected pieces of information 380, 381, 382, 383 and 384 are stored as new data of the classification model in the classification model storage unit 352 and, at the same time, the image data 371 and 372 are stored additionally in the image data storage unit 350 to construct an image date base.

A defect which cannot be identified is indicated for the operator by the terminal equipment 311 and is added to the image data base and is registered as a classification model. The detected pieces of information 380, 381, 382, 383 and 384 are stored as the data of new classification models in the classification model storage unit 352. The image data corresponding to the data of the new classification models is added to the contents of the image data storage unit 350 to construct an image data base. A defect which cannot be identified is indicated for the operator by the terminal equipment 311 and is added to the image data base and is registered as classification model.

Although the foregoing description is based on an assumption that the comparison is made in the n-dimensional feature data space, the comparison may be made on the basis of the correlation between the image of the defect, and a representative defect mode contained in the image data base or a plurality of images of defects, using the image data base stored in the image data storage unit 350.

When storing an image in the image data storage unit 350, data representing the condition of the manufacturing process, i.e., parameters for controlling a wafer manufacturing apparatus, which will be described later,, and information about other inspection units or monitors are stored in the image data storage unit 350.

The foregoing procedure for defect classification and feature data extraction can be repeatable whenever necessary by reading the image data because the image data 371 and 372 of defects are held by the image data storage unit 350. Since the condition of the manufacturing process at that time can be read from the image data storage unit 350 and can be displayed on the terminal equipment 311, both the defects and the condition of the manufacturing process can be known.

Figure 8:
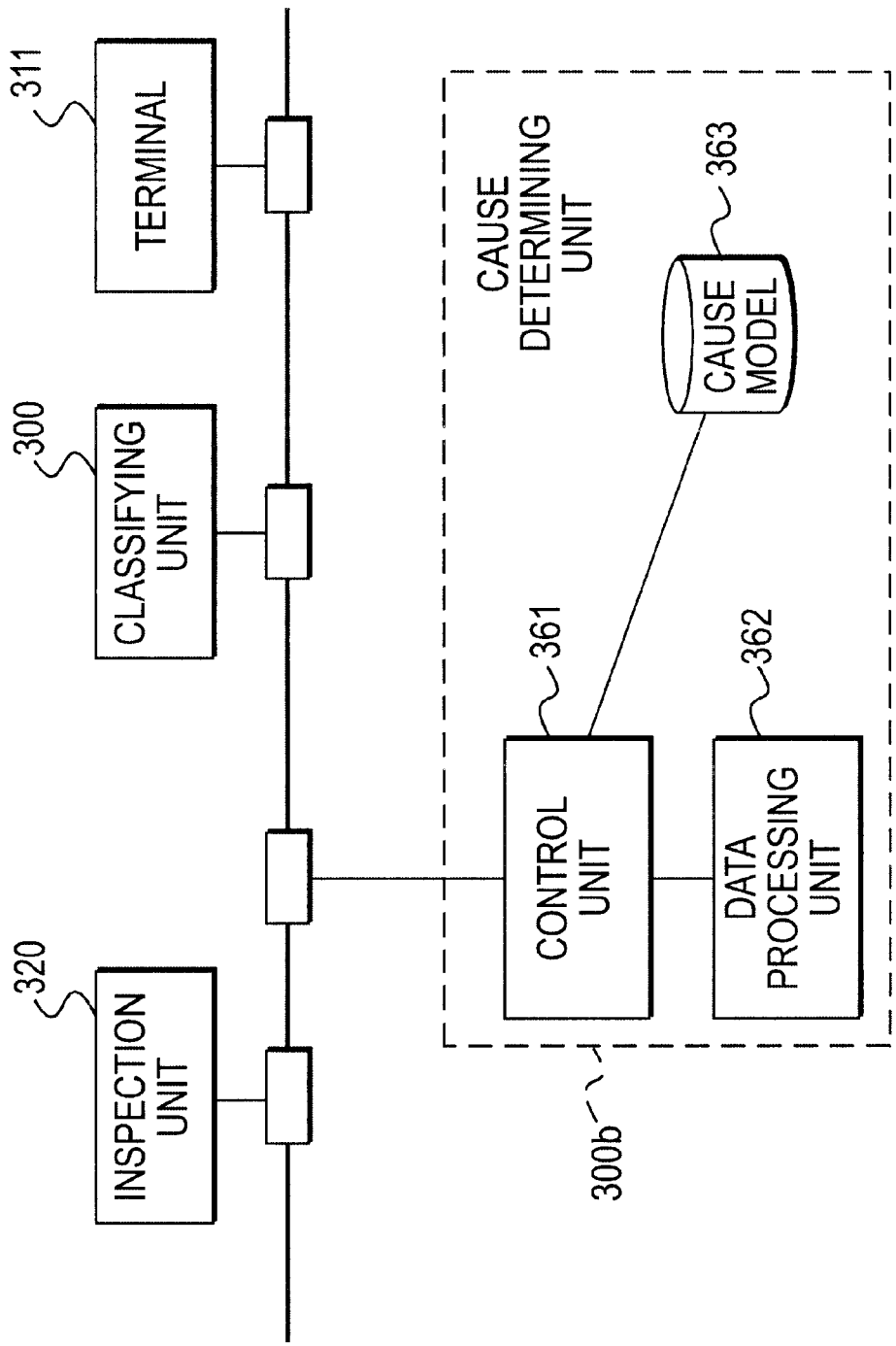
FIG. 8 is a block diagram of a cause determining unit.

The result of defect classification and the feature data information on which defect classification is based are given to the cause determining unit 300b. FIG. 8 shows the configuration of the cause determining unit 300b. The cause determining unit 300b comprises a control unit 361, a data processing unit 362, and cause models 363 to be used for determining causes of defects from the result of defect classification. The control unit 301 and the data processing unit 302 of the classifying unit 300 of FIG. 3 may be used as the control unit 361 and the data processing unit 362, and the cause models 363 may be connected to the control unit 301.

Figure 9:
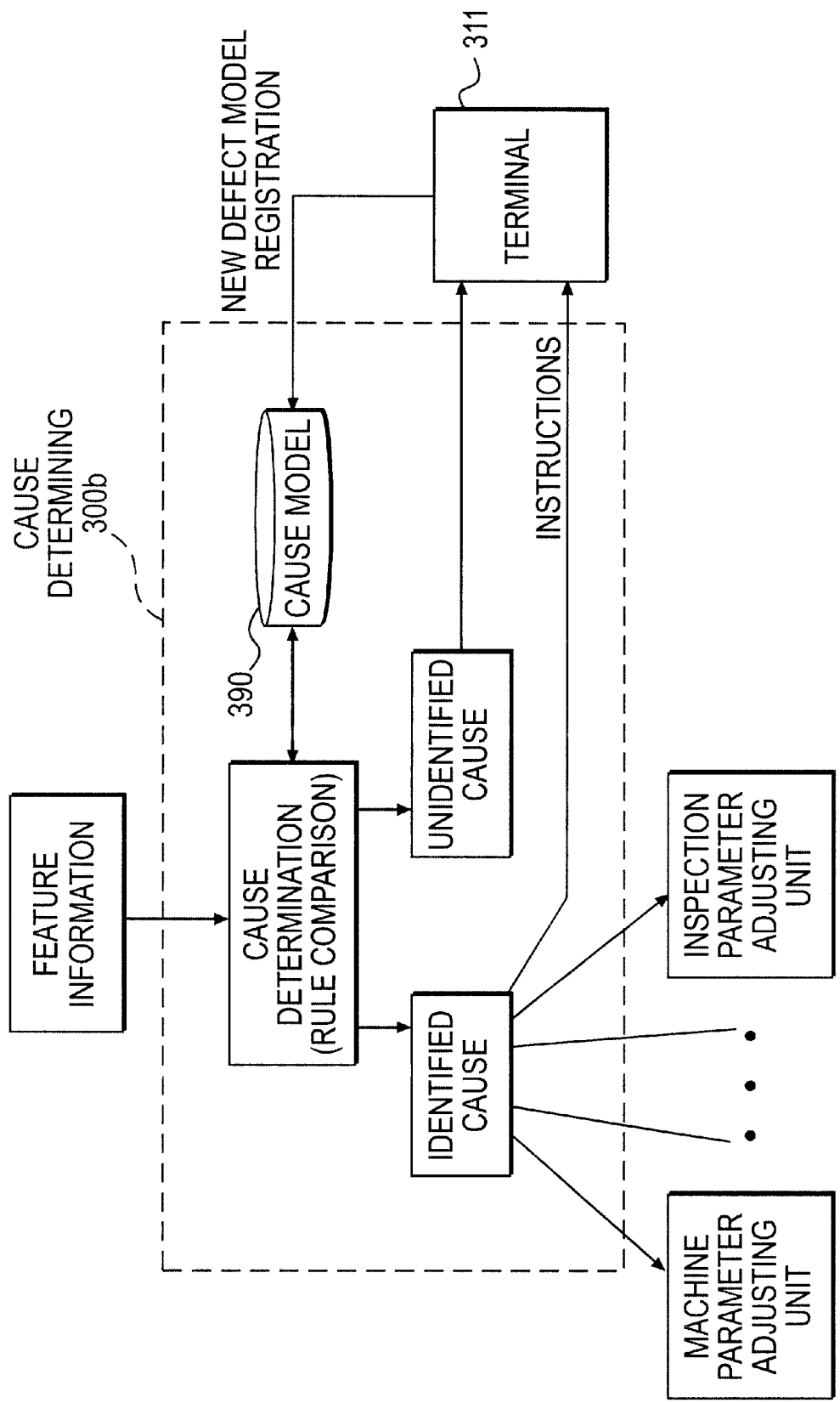
FIG. 9 is a conceptual block diagram of assistance in explaining a procedure for determining causes of defects.
Figure 10:
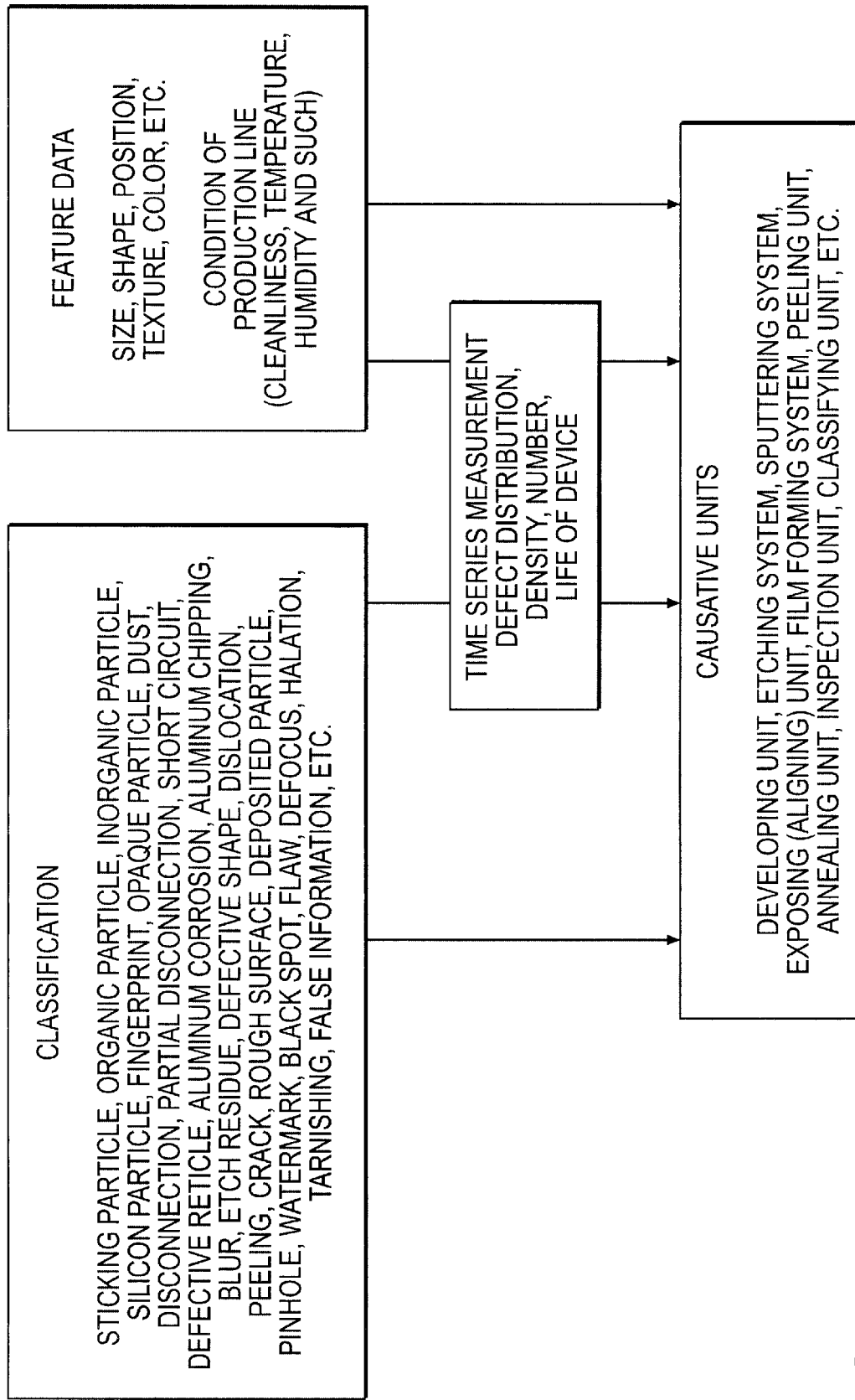
FIG. 10 is a conceptual block diagram of a cause model.

Referring to FIG. 9, when determining the cause of a defect, the result of defect classification provided by the classifying unit 300 and the feature data information on which defect classification is based are compared with the cause models 390 to identify the cause of the defect. If the cause of the defect cannot be identified, information is indicated to that effect on the terminal equipment 311 and a new cause model is registered. The cause models 390 are those as shown in FIG. 10. Information about the cleanliness of the entire manufacturing process, time series defect information and the distribution of defects are used in combination with the result of classification of individual defects to specify an apparatus causative of the defect, and the result of defect classification and the feature data information on which the defect classification is based are given to machine parameter adjusting units 331, 332, 333 and 334, which will be described later. The same information is given to an inspection parameter adjusting unit 330 for the adjustment of the inspecting standards for the operation of the inspection unit.

The inspection parameter adjusting unit 330 for converting the result of defect classification and the feature data information on which defect classification is based into inspecting standards for the inspection unit, and the machine parameter adjusting units 331, 332, 333 and 334 for converting the same information into control parameters for controlling the manufacturing machine will be described below.

Figure 11:
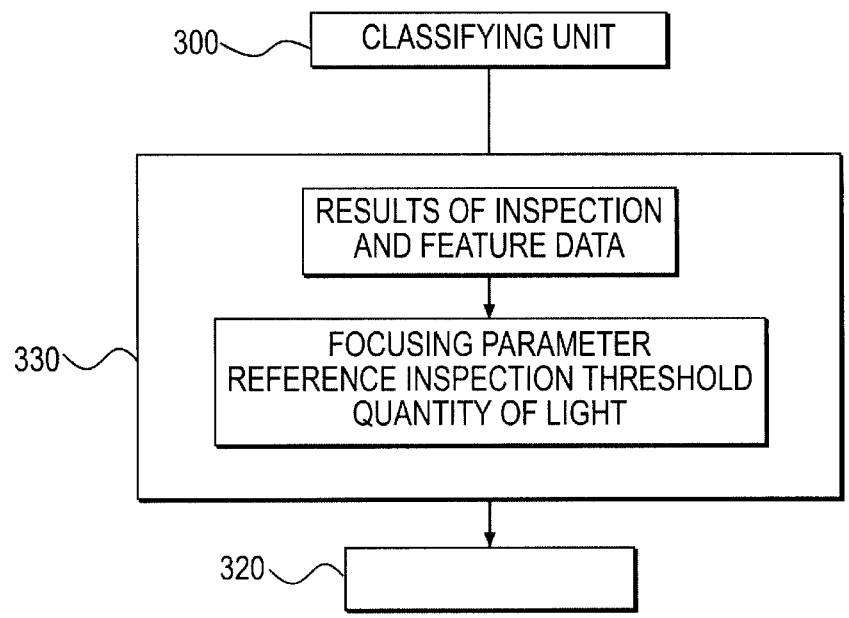
FIG. 11 is a conceptual block diagram of assistance in explaining a method of adjusting and controlling an inspection unit.

Referring to FIG. 11, when the inspection unit does not leave any defect undetected but many pieces of false information are provided, the inspection parameter adjusting unit 330 adjusts process parameters so as to meet the level of the machine. If much false information is attributable to mechanical troubles, an indication is displayed to that effect on the terminal equipment 311 to the operator. If the inspection unit leaves some defects undetected, the inspection parameter adjusting unit 330 adjusts the thresholds of the inspecting standards. If failure in detection of defects is attributable to the defocusing of the image sensing unit of the detector, the inspection parameter adjusting unit 330 adjusts focusing parameters. If illumination is causative of failure in detection of defects, the inspection parameter adjusting unit 330 adjusts the luminance of the illuminating unit 346.

Figure 12:
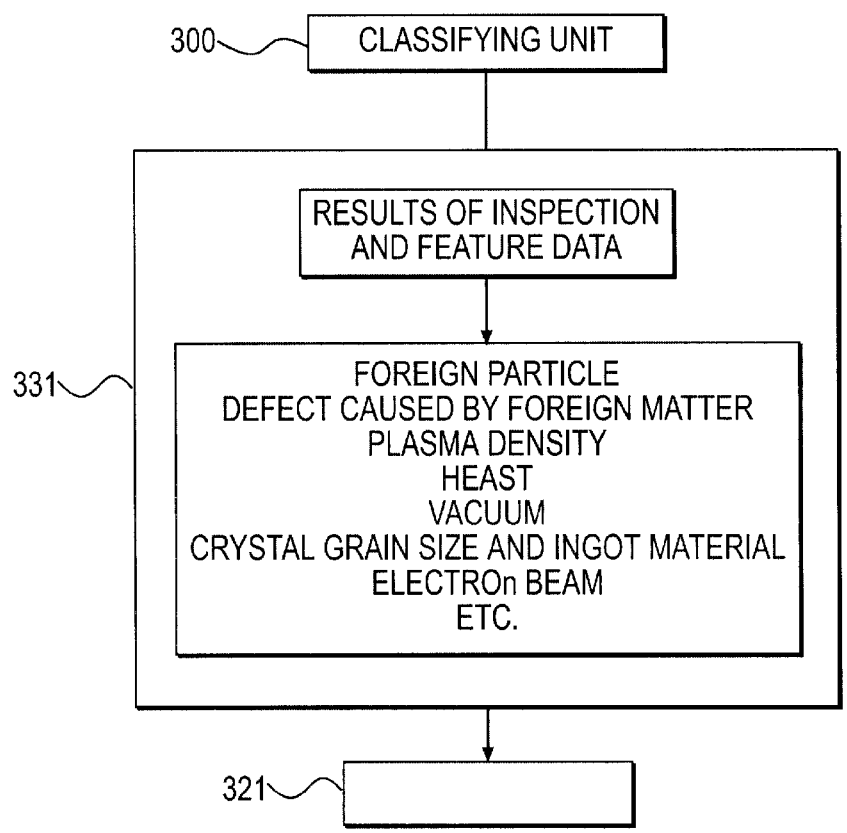
FIG. 12 is a conceptual block diagram of assistance in explaining a method of adjusting and controlling a film forming apparatus.

When the defect is caused by the film forming unit 321, the machine parameter adjusting unit 331 converts the result of defect classification and the feature data information on which defect classification is based into control parameters as shown in FIG. 12 for controlling the manufacturing machine, and the film forming unit 321 is adjusted and controlled.

Figure 13:
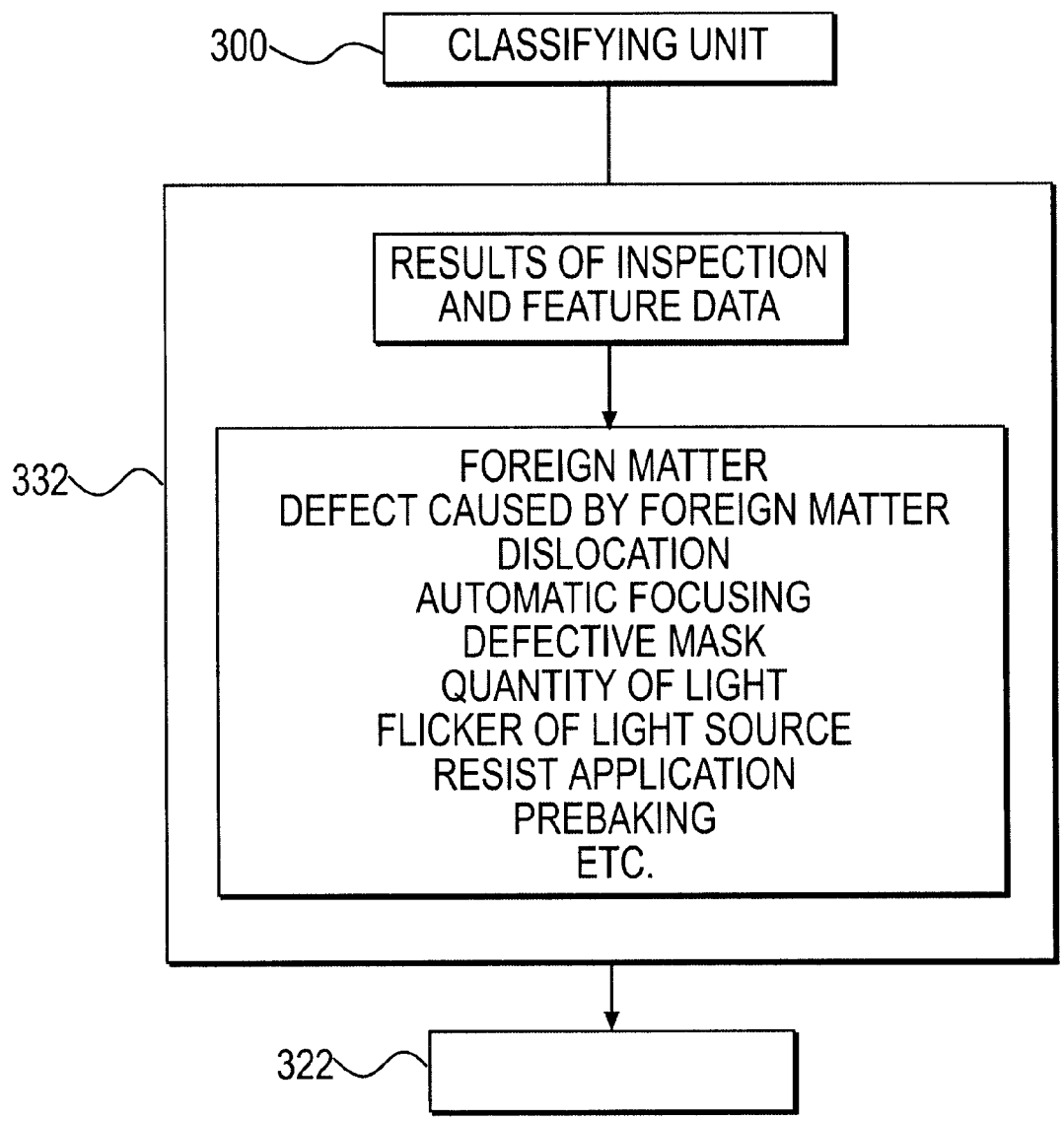
FIG. 13 is a conceptual block diagram of assistance in explaining a method of adjusting and controlling an exposure unit.

When the defect is caused by the exposure unit 322, the machine parameter adjusting unit 332 converts the result of defect classification and the feature data information on which defect classification is based into control parameters as shown in FIG. 13 for controlling the manufacturing machine, and the exposure unit 322 is adjusted and controlled. If the defect is caused by a mechanical malfunction, the parameters are not adjusted and information that there is mechanical trouble is indicated on the terminal equipment 311 to prompt the operator to repair the relevant machine.

When the defect is caused by a defective mask, the terminal equipment 311 prompts the operator to change the defective mask, instructions about measured to remove causative foreign matters and flaws are given to the operator, information is given to the process control system 335 to that effect and, if the adhesion of the foreign matters to the mask is due to the condition of the entire process, a control process control system provides instructions to clean the whole manufacturing process.

Figure 14:
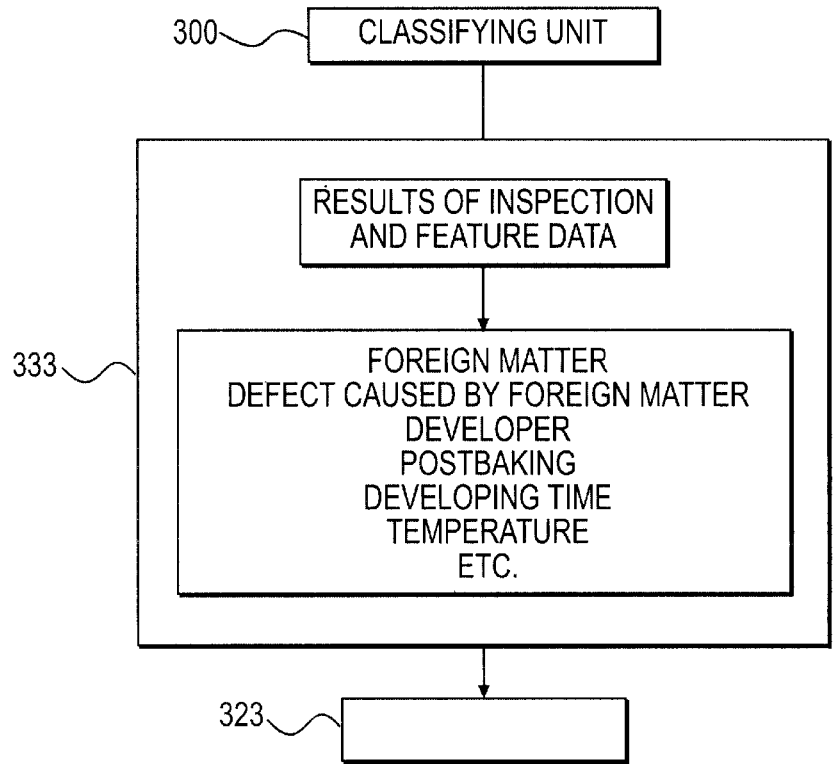
FIG. 14 is a conceptual block diagram for explaining a method of adjusting and controlling a developing unit.

When the defect is caused by the developing unit 323, the machine parameter adjusting unit 331 converts the result of defect classification and the feature data information on which defect classification is based into parameters as shown in FIG. 14 for controlling the manufacturing machine to adjust and control the developing unit 323.

Figure 15:
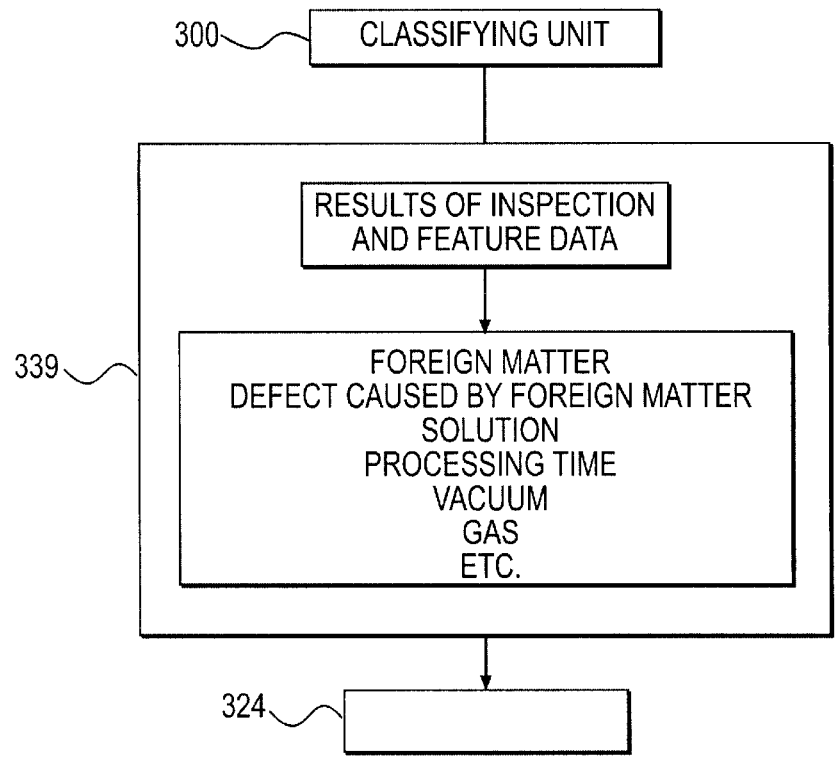
FIG. 15 is a conceptual block diagram for explaining a method of adjusting and controlling an etching unit.
Figure 16:
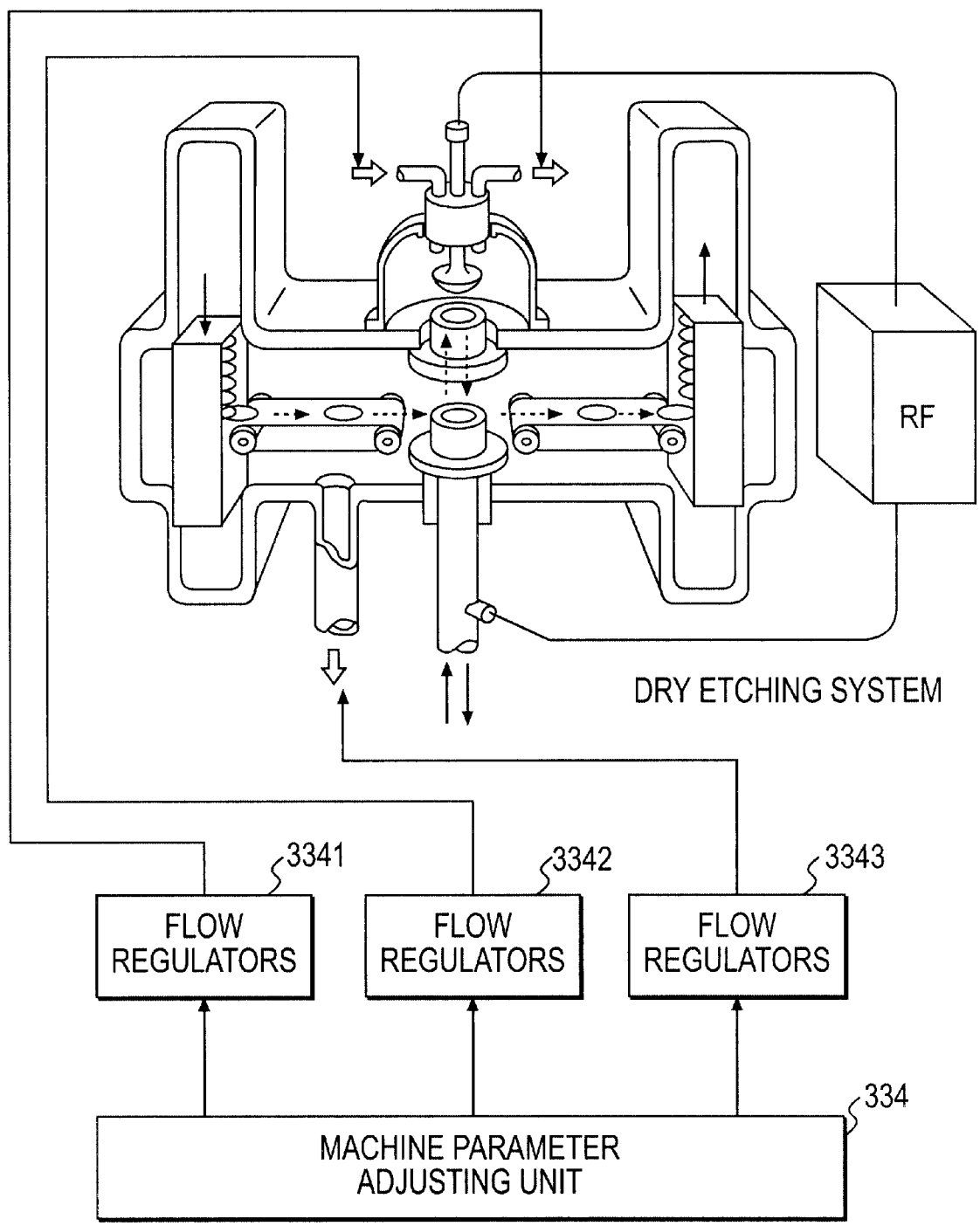
FIG. 16 is a schematic view for explaining a method of adjusting and controlling a dry etching unit.

When the defect is caused by causes as shown in FIG. 15 in the etching unit, the machine parameter adjusting unit 334 adjusts the concentration of the solution if the etching unit is of a wet etching system or the flow rates of gases are adjusted through the machine parameter adjusting unit 334 by flow regulators 3341, 3342 and 3343 if the etching unit is of a dry etching system as shown in FIG. 16.

Figure 17:
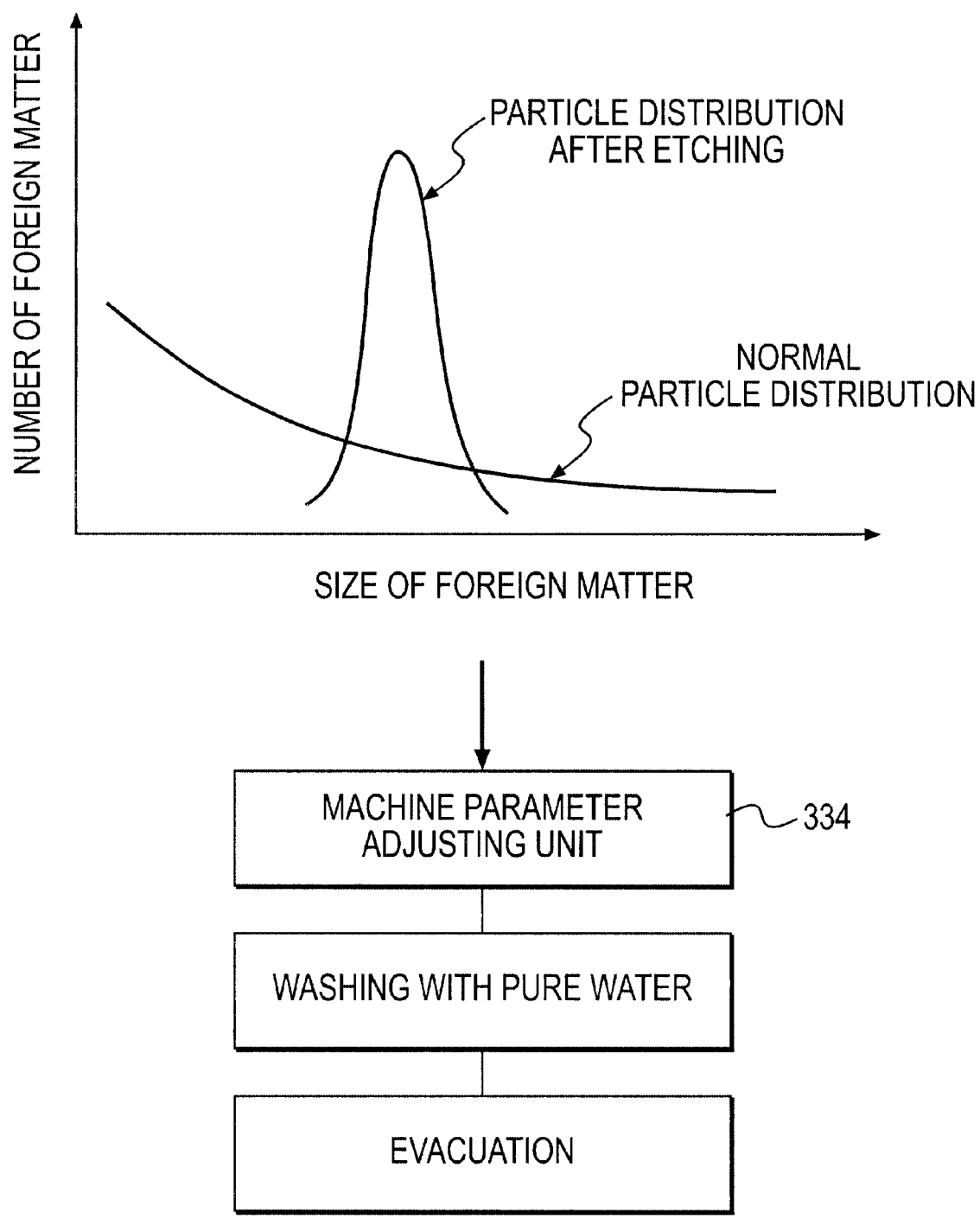
FIG. 17 is a diagram of for explaining a method of adjusting and controlling an etching unit when the etching unit malfunctions.

As shown in FIG. 17, the distribution of particles, i.e., foreign matters, introduced into the product by the etching unit is different from that of particles introduced into the product in a steady state; that is, particles are distributed in a narrow range of particle size, so that it can easily be determined that the etching unit introduced those particles into the product. In such a case, the machine parameter adjusting unit 334 gives an order to wash the interior of the etching unit with pure water, and then the etching unit is evacuated for self cleaning. It is also possible to make such a determination on the basis of the shape and the distribution on the product of particles.

Figure 18:
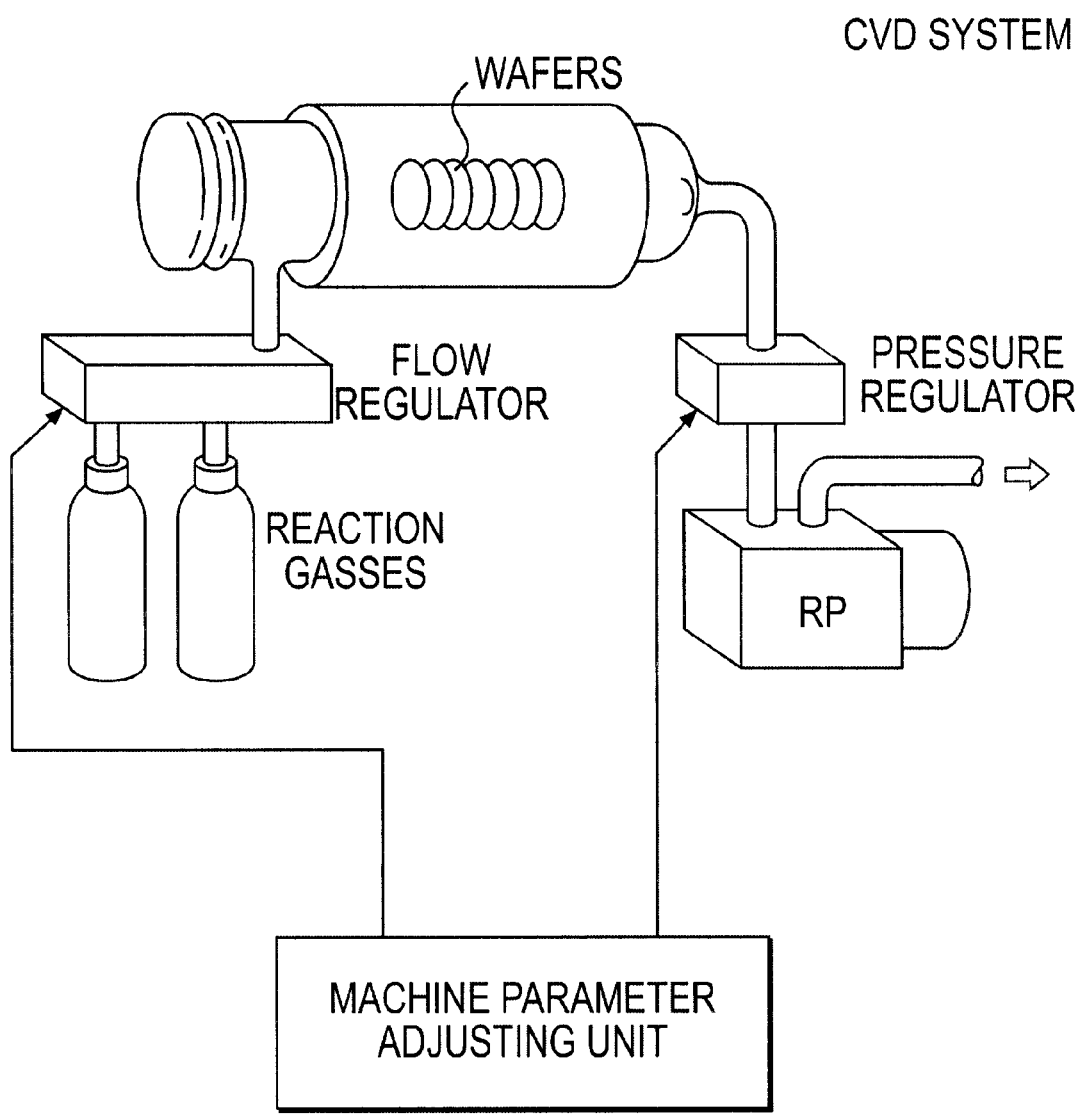
FIG. 18 is a schematic perspective view for explaining a method of adjusting and controlling a CVD system.

In a CVD system as shown in FIG. 18, the machine parameter adjusting unit gives information to a flow regulator and a pressure regulator to control the flow rates and the pressures of the gases.

Naturally, plans for the maintenance of and conditions for the operation of the manufacturing machines including an annealing unit, an ion implantation unit, an evaporating unit and an electrical inspection unit as well as the aforesaid manufacturing machines can be worked out on the basis of the result of defect classification and information extracted from the classified defects by the aforesaid methods.

There have been described above about the functions of the inspection parameter adjusting unit 330 for converting the result of defect classification and the feature data information on which defect classification is based into inspecting standards for discriminating between defective and nondefective products by the inspection unit, and the machine parameter adjusting units 331, 332, 333 and 334 for converting the same information into control parameters for controlling the manufacturing machines. The result of defect classification and the feature data information on which defect classification is based may be defect categories and parameters of feature data models stored in the classification model storage unit 352. When the defect categories and the parameters of feature data models are used, stable, highly accurate statistical information can be given to the inspection parameter adjusting unit 330 and the machine parameter adjusting units 331, 332, 333 and 334, and hence the manufacturing process can be maintained in a further stable state.

When the results of inspection or information on which inspection is based is engraved in the marginal areas of each wafer or each chip with, for example, a laser beam, by an information attaching unit 399 of FIG. 2, investigation into causes of defects developed between the successive testing processes is possible. If the information is engraved on each chip, investigation into the correlation between the results of electrical inspection, such as inspection for fail bits after dicing, and defects attributable the manufacturing process is possible.

An inspection system in a second embodiment according to the present invention including an automatic inspection unit for detecting foreign matters adhering to semiconductor wafers employing an invention disclosed in Japanese Patent Laid-open (Kokai) No. 54-101390 will be described hereinafter.

Figure 19:
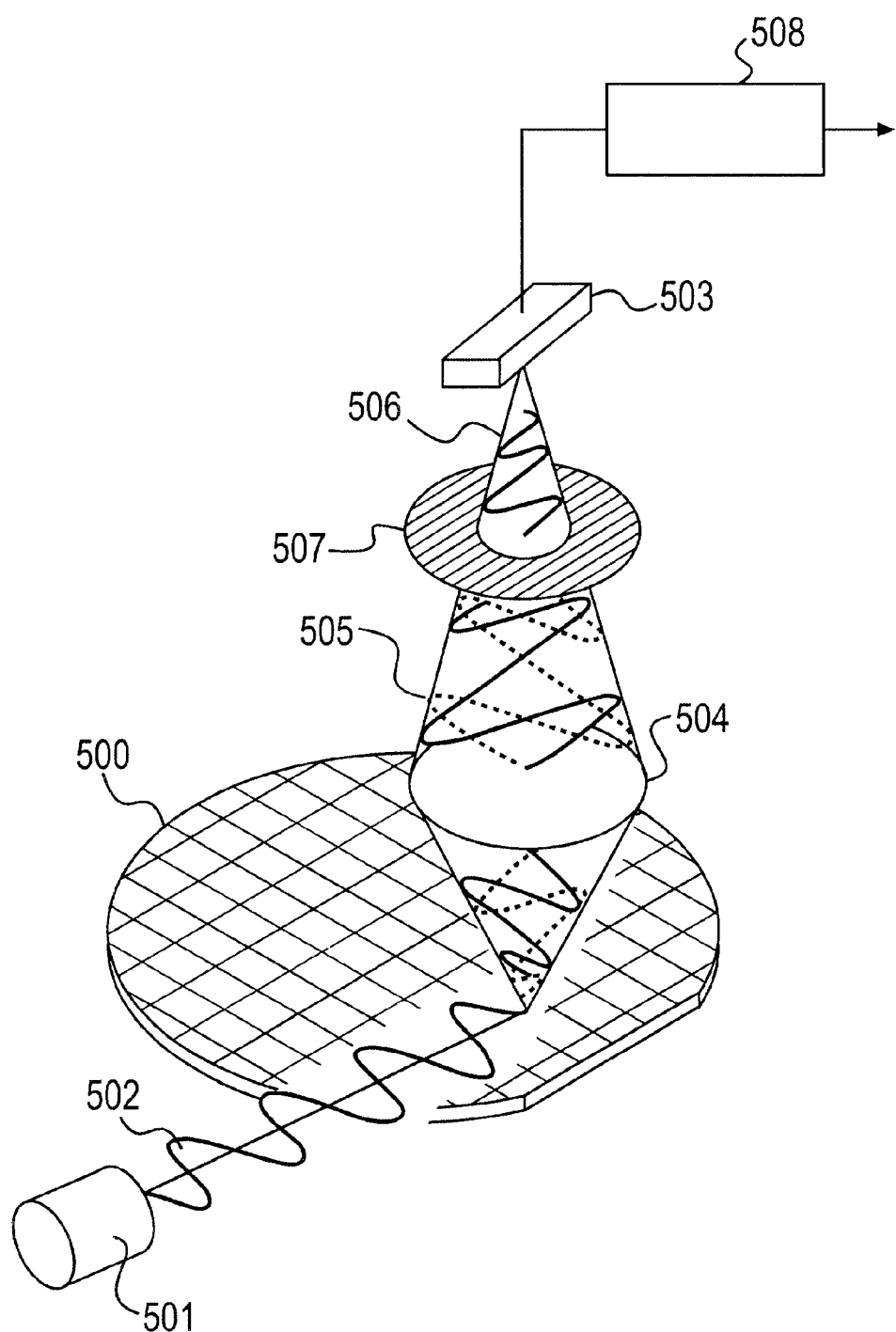
FIG. 19 is a schematic perspective view for explaining the principle of detecting foreign matters on a wafer.

Referring to FIG. 19 showing the principle of detection according to the aforesaid disclosed invention, a laser light source 501 project S-polarized laser beam 502 on the surface of a semiconductor wafer 500, i.e., a product, so that the laser beam 502 falls on the surface of the semiconductor wafer 500 at an angle nearly equal to zero to the surface of the semiconductor wafer 500. The laser beam 502 reflected vertically upward is detected by a detector 503. The major component of the laser beam scattered by a pattern formed on the semiconductor wafer 500 is S-polarized laser beam and the minor component of the same is P-polarized laser beam, where as the most component of laser beam scattered by a particle adhering to the wafer is P-polarized laser beam. The vertically reflected laser beam is focused on the detector 503 with a focusing lens 504.

In FIG. 19, broken lines indicate the laser beam scattered by the pattern formed on the semiconductor wafer 500, and continuous lines indicate scattered laser beam scattered by the particle adhering to the semiconductor wafer 500. Most part of the laser beam scattered by the pattern and traveled through the focusing lens 504 is intercepted by a polarizing plate 507 for selectively absorbing S-polarized laser beam, so that the detector 503 is able to detect only the laser beam scattered by the particle adhering to the semiconductor wafer 500 in a high accuracy. A signal processing circuit 508 processes the output signals of the detector 503 to detect the particle. Upon the detection of the particle, the signal processing circuit 508 provides a position signal representing the position of the particle on the semiconductor wafer 500.

Figure 20:
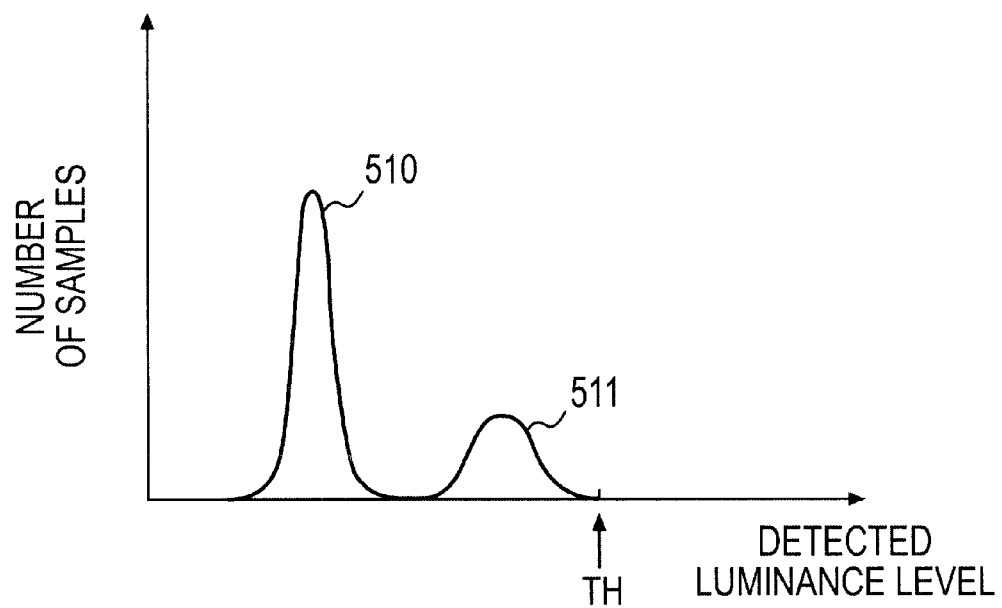
FIG. 20 is a graph of data obtained by inspecting a wafer carrying 1 μm standard particles.

FIG. 20 is a graph typically showing distribution curves of detected luminance levels determined by inspecting the surface of a wafer carrying a 1 µm standard particle by the foregoing inspecting method. Indicated at 510 is a cluster of a pattern formed on the wafer and at 511 is a cluster of the 1 µm standard particle. Although the luminance of the beam scattered by the pattern formed on the wafer and detected by the detector is low, a comparatively high peak appears at a comparatively low luminance level because the ratio of the surface area of the pattern to the surface area of the wafer is greater than that of the particle. On the other hand, although the ratio of the surface area of the 1 µm standard particle to the surface area of the wafer is small, the distribution of the luminance of the scattered light scattered by the 1 µm standard particles, i.e., a foreign matter, has a comparatively low peak at a comparatively high luminance level because the luminance is high.

Figure 21:
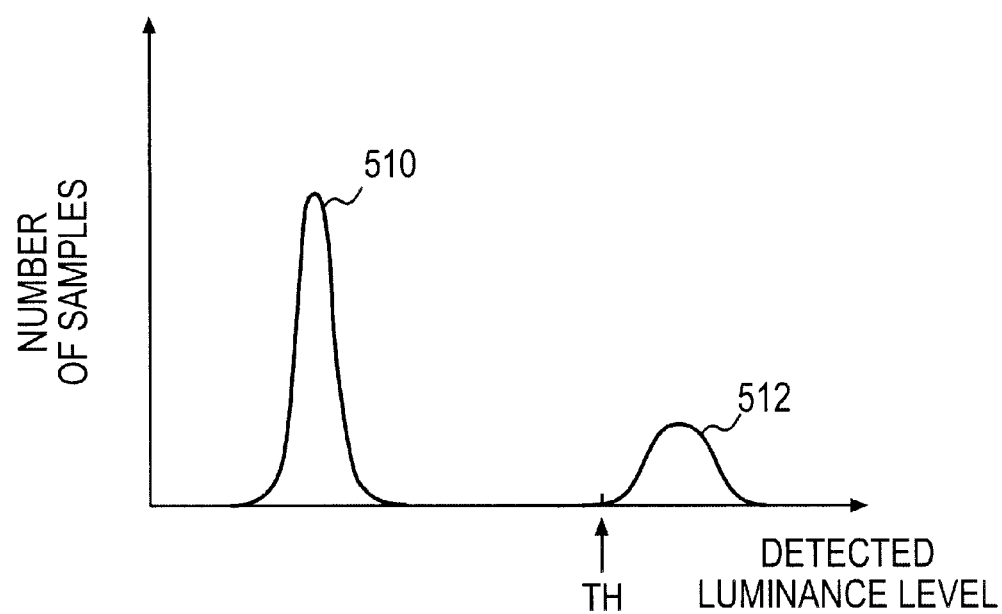
FIG. 21 is a graph of data obtained by inspecting a wafer carrying 2 μm standard particles.

FIG. 21 is a graph typically showing distribution curves of detected luminance levels determined by inspecting the surface of a wafer carrying a 2 µm standard particle. Since the scattering area of the 2 µm standard particle is greater than that of the 1 µm standard particle, the luminance level at which a peak appears in the distribution curve for the 2 µm standard particle is higher than that at which a peak appears in the distribution curve for the 1 µm standard particle. Accordingly, when it is desired to detect only foreign matters of sizes greater than a given size, a threshold luminance level is set. If a threshold luminance level TH as shown in FIGS. 20 and 21 is set, only foreign matters of sizes not smaller than 2 µm can be detected. The threshold luminance level TH is determined according to the size of foreign matters to be detected for process control. The threshold luminance level TH is a control parameter for controlling the sensitivity of the foreign matter detector.

The sensitivity can be controlled by controlling the detection system; that is, when the current supplied to a driver for driving the laser beam source is controlled to regulate the intensity of the laser beam emitted by the laser beam source, the detection luminance level can be regulated accordingly, which will be explained with reference to FIGS. 22 and 23.

Figure 22:
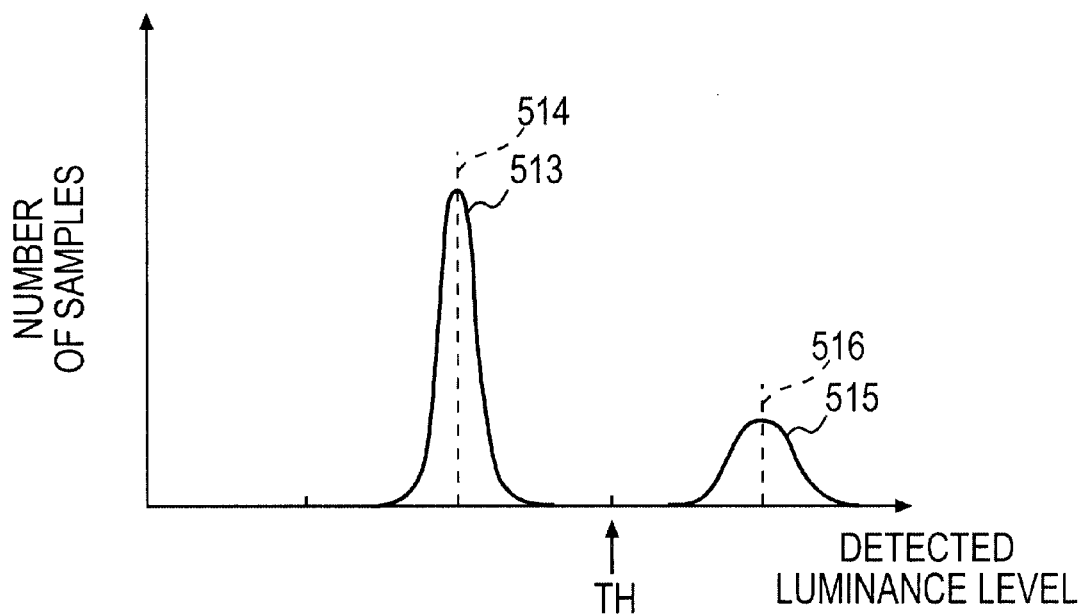
FIG. 22 is a graph of data obtained by inspecting a wafer carrying 1 μm standard particles.

FIG. 22, similarly to FIG. 20, is a graph typically showing distribution curves of detected luminance levels determined by inspecting the surface of a wafer carrying a 1 µm standard particle by the foregoing inspecting method, in which a current $I_0$ was supplied to the driver for controlling the laser beam source.

Figure 23:
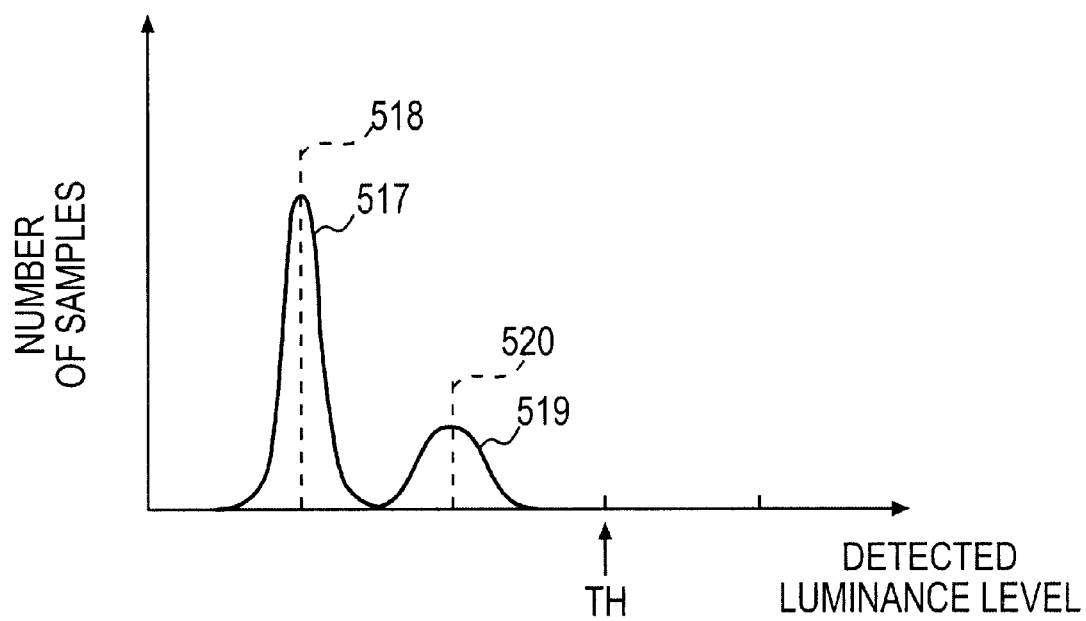
FIG. 23 is a graph of data obtained by inspecting a wafer carrying 1 μm standard particles, in which the intensity of the laser beam is half that of the laser beam used for obtaining the data shown in FIG. 22.

FIG. 23 is a graph typically showing distribution curves of detected luminance levels determined by inspecting the surface of a wafer carrying a 1 µm standard particle when a current $I_1$ that makes the laser beam source emit laser beam of an intensity half the intensity of laser beam emitted by the laser beam source when a current $I_1$ is supplied to the driver is supplied to the driver.

As shown in FIGS. 22 and 23, the central value 518 of a cluster 517 of a pattern formed on a wafer is half the central value 514 of a cluster 513 of the pattern, and the central values 520 of a cluster 519 of the 1 µm standard particle is half the central value 516 of a cluster 515 of the 1 µm standard particle, because the intensity of the laser beam is reduced by half and the detected luminous level is reduced accordingly when the current I supplied to the driver for controlling the laser beam source is reduced from $I_0$ to $I_1$. Therefore, when a fixed threshold luminance level TH is given as shown in FIGS. 22 and 23, a foreign matter of a size can be detected when the current supplied to the driver for controlling the laser beam source is $I_0$ and the same particle cannot be detected when the current $I_1$ is supplied to the driver. Thus, the detection sensitivity of the detector can be regulated by regulating the current supplied to the driver for controlling the laser beam source. The detection sensitivity can be regulated also by regulating the gain of the detector.

The defect classifying and feature extracting unit 2 (FIG. 1) reads an image of the semiconductor wafer, i.e., the product, on the basis an output of the automatic inspection unit representing the coordinates of the position of the foreign matter on the semiconductor wafer. Since the semiconductor wafer has a plurality of identical nondefective chips or a plurality of identical nondefective patterns in addition to the identical defective chip or the identical defective pattern, an image of the nondefective chip or the nondefective pattern is used as a reference image, the reference image is subtracted from the image of the defective chip or the defective pattern by the method disclosed in Denshi Joho Tsushin Gakkai Ronbunshi (Journal of Electronic Information Communication Society) D-II, Vol. J72-D-II, No. 12, pp. 2041–2050 to extract only the image of the foreign matter, and then the area of the image of the foreign matter is measured to determine the size of the foreign matter. This procedure is carried out for the outputs of the automatic inspection unit provided by detecting one semiconductor wafer, and then the sizes of foreign matters are classified to determine the distribution of the sizes of the foreign matters.

In view of this result, the operator operates the defect classification indicating unit 6 shown in FIG. 1 connected to the defect classifying and feature extracting unit to enter the size of a foreign matter to be detected. The feature data converting unit 3 shown in FIG. 1 may be provided with an arithmetic circuit of a processing system realizing Z=F(S), where Z is conversion output and S is area, in order that the input area is converted into the threshold luminance level TH shown in FIGS. 20 and 21, the current for controlling the intensity of the laser beam, or the value for controlling the gain of the detector. In another system, the feature data converting unit 3 shown in FIG. 1 may be a look-up table that provides an output Z, i.e., the threshold luminance level TH shown in FIGS. 20 and 21, the current for controlling the intensity of laser beam or the value for controlling the gain of the detector, corresponding to the area S.

When the defect classifying and feature extracting unit 2 shown in FIG. 1 has the function explained in connection with the foregoing example of inspection of a defect in the pattern formed on a wafer, the extracted information about foreign matters can be applied to the manufacturing process for the same effect.

Figure 24:
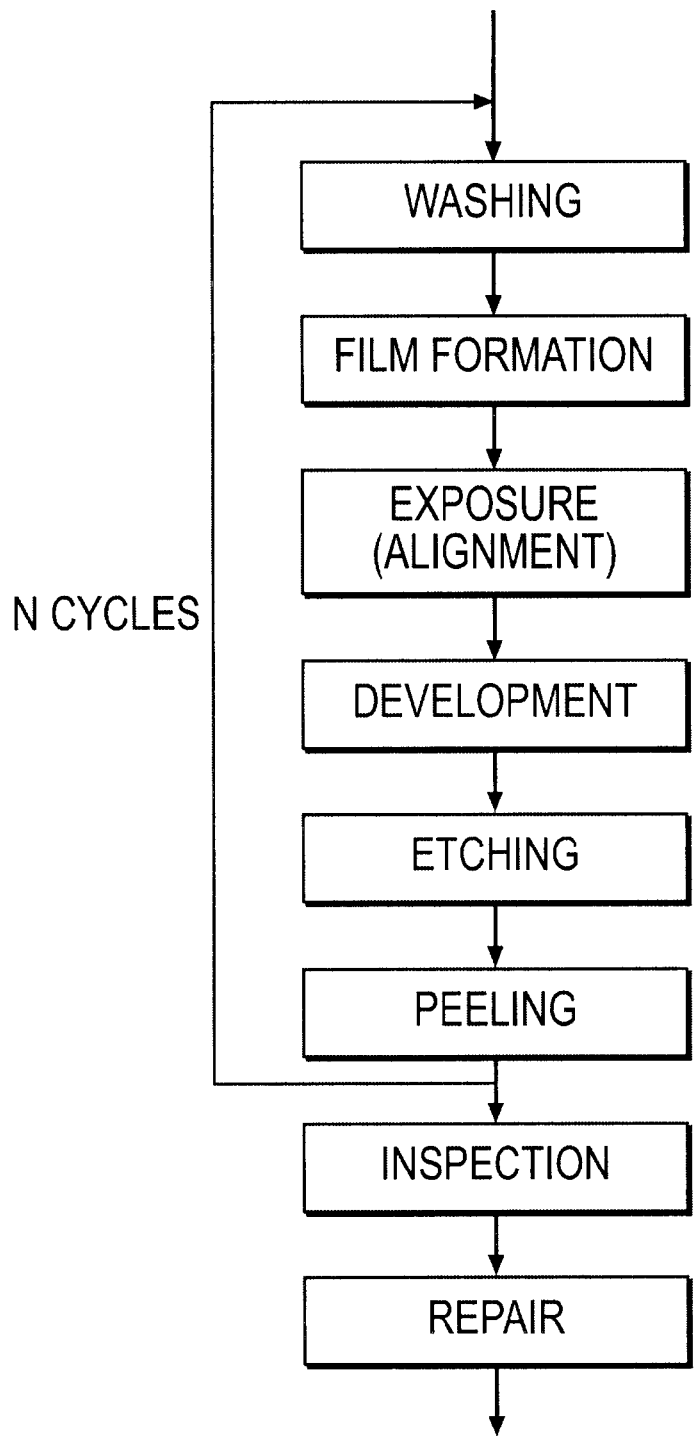
FIG. 24 is a flow chart of a thin-film transistor wafer manufacturing process.
Figure 25:
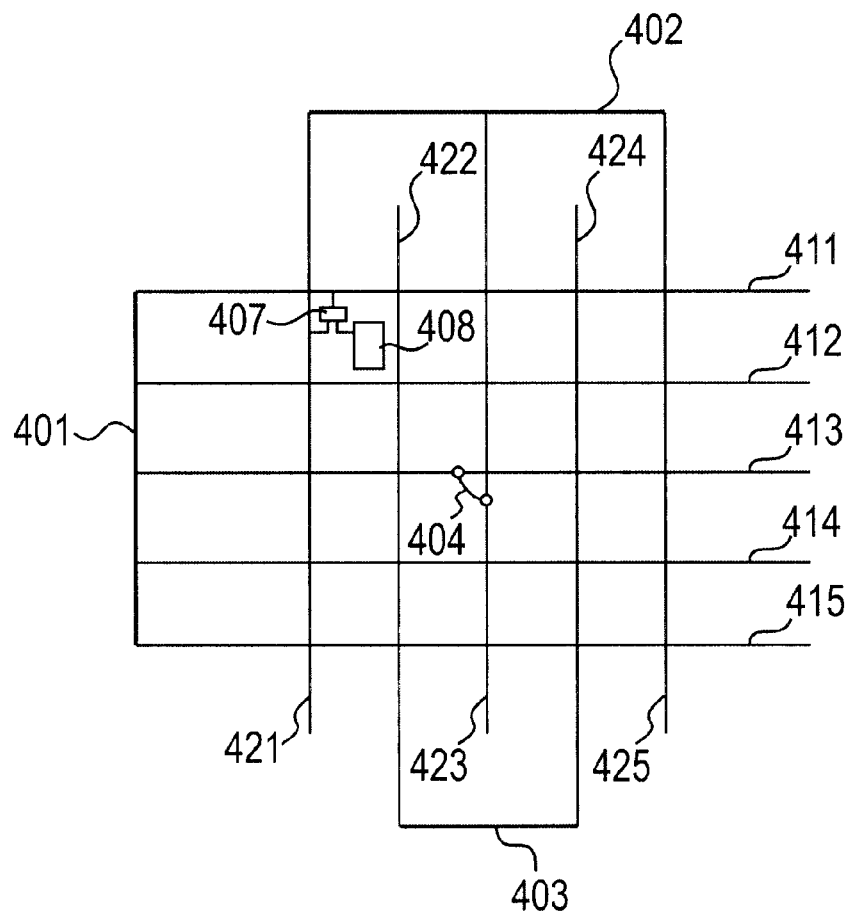
FIG. 25 is a typical wiring diagram of the electrical configuration of a thin-film transistor wafer.

An embodiment of the present invention applied to a process of manufacturing a thin-film transistor wafer for a liquid crystal display will be described hereinafter. FIG. 24 shows a manufacturing process for manufacturing the thin-film transistor wafer. Basically, this manufacturing process is the same as the semiconductor wafer manufacturing process, except that the inspection step in this manufacturing process gives priority to the inspection of electric circuits over the inspection of appearance. All the product is inspected for short-circuiting defects and, if the products have defects, the defective products are repaired. FIG. 25 is a typical wiring diagram showing the electrical wiring of a thin-film transistor wafer. The thin-film transistor wafer is provided with gate lines (G-lines) 411 to 415, drain lines (D-lines) 421 to 425 extending across and insulated from the G-lines. A thin-film transistor 407 and a transparent photocathode 408 are formed at each of intersections of the G-lines and the D-lines.

The G-lines are connected to a common line 401, and the D-lines are connected to common lines 402 and 403 to prevent electrostatic breakdown until the thin-film transistor wafer is completed. In this example, a short-circuiting defect 404 is the short-circuiting of the G-line and the D-line causing linear faulty indication, which is a critical defect in the thin-film transistor wafer. Therefore, the detected short-circuiting defect 404 is cut off with a laser beam to disconnect the G-line and the D-line electrically. It is possible that the D-lines are short-circuited by a short-circuiting defect. This short-circuit defect is also cut off with a laser beam to disconnect the D-lines electrically.

Figure 26:
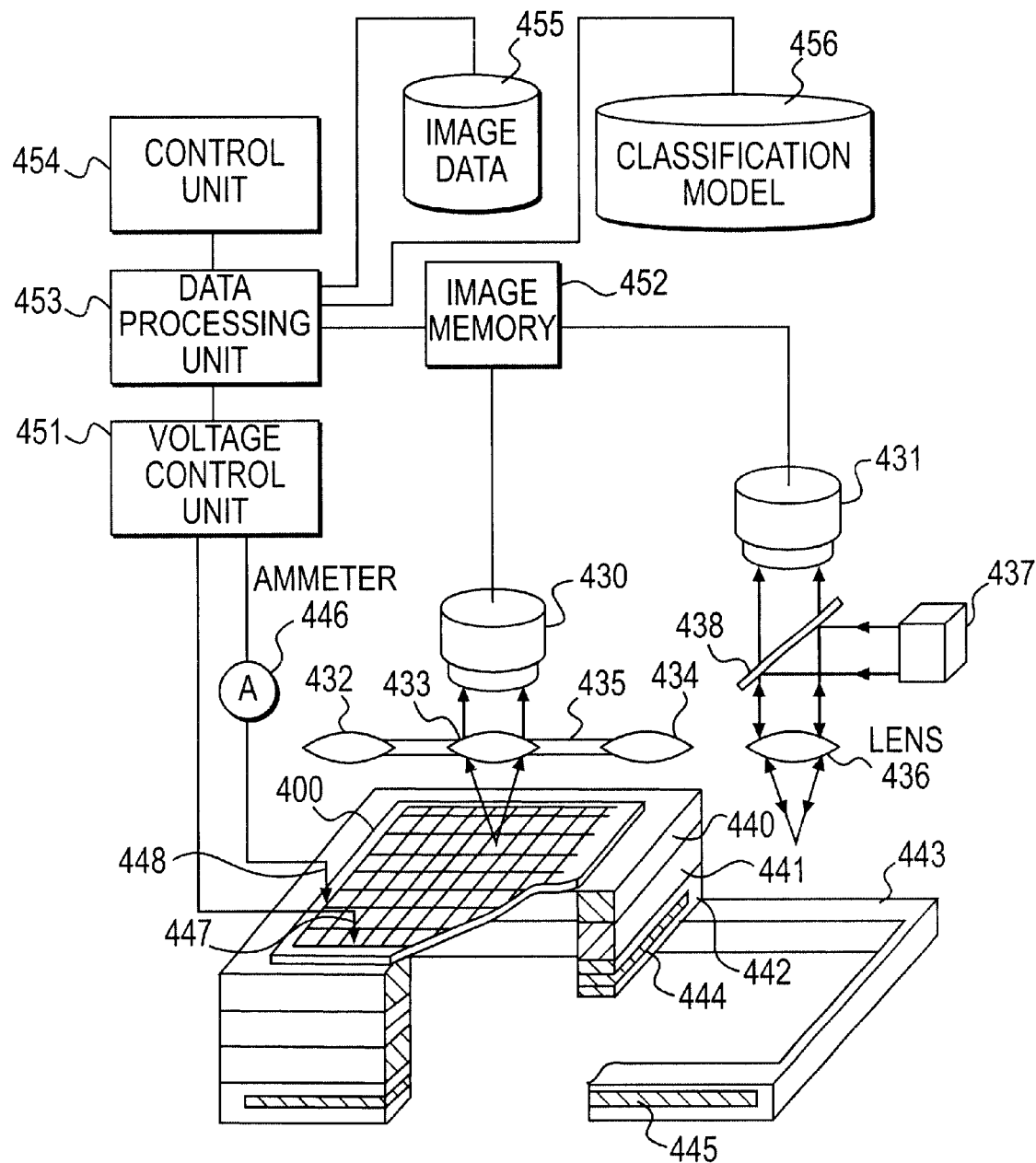
FIG. 26 is a block diagram of a short circuit inspecting and repairing apparatus having a defect classifying function.

FIG. 26 shows a wafer inspecting system for detecting short-circuiting defects and repairing a short-circuited circuit, capable of defect classification. A thin-film transistor wafer 400 is mounted on a composite stage consisting of a θ-stage 440, a Z-stage 441, a Y-stage 442 provided with a positioning sensor 444, and an X-stage 443 provided with a positioning sensor 445. Wafer probers 447 and 448 are applied respectively to the common lines 401 and 402, the common lines 401 and 403 or the common lines 402 and 403 shown in FIG. 25. A voltage control unit 451 controls voltage applied across the wafer probers 447 and 448 while current is monitored by an ammeter 446. Heat generated by the current flowing through the short-circuiting defect 404 is detected by an infrared detector 430 to measure the radiated infrared rays as image information. The infrared detector 430 is provided with lenses 432, 433 and 434. A desired one of the lenses 432, 433 and 434 can be set at a working position by a revolver 435.

The image information thus acquired is stored in the image memory 452 and processed to determine the position of the short circuit defect 404. The stage 443 is moved according to the position information about the position of the short-circuiting defect 404. The defect is observed and the short-circuiting line is cut off by a microscopic laser processing unit comprising a detector 431, a half mirror 438, a lens 436 and a laser oscillator 437, and serving as a microscope and a laser processing device. Feature data is extracted from the image information obtained by the detector 431 and the image information obtained by the infrared detector 430, the feature data is compared with a classification models 456 to determine the type of the defect. This procedure can be achieved by a method similar to the wafer inspecting method previously described with reference to FIGS. 4 and 9.

In the inspection of the thin-film transistor wafer for a liquid crystal display, which is different from inspection for the observation of appearance, even most visually unobservable short-circuiting defects can be observed in infrared images. The present invention is applicable to inspection using an optical system using a radiation of a wavelength different from that of a radiation used by an ordinary optical system. After the category of the defect has been determined, information is given to the cause determining unit, information is given to the process control system, the machine parameter adjusting unit and the inspection parameter adjusting unit, and the stored image data 455 and the stored classification models 456 are updated. The parameter, such as the detection wavelength used by the wafer inspecting system, can be changed by the inspection parameter adjusting unit on the basis of the data provided by the cause determining unit.

Figure 27:
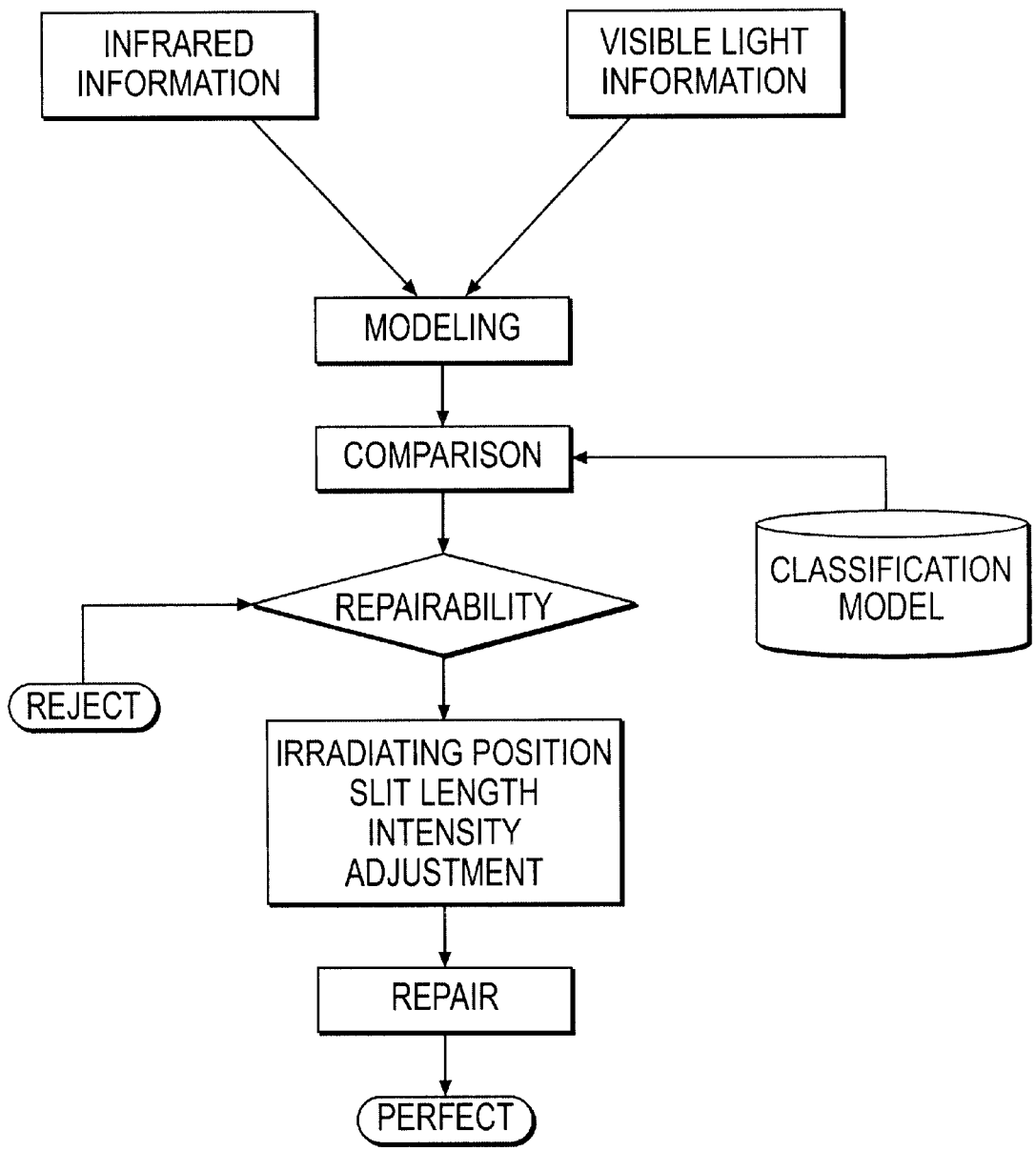
FIG. 27 is a flow chart of a repairing procedure to be carried out by the short circuit inspecting and repairing apparatus of FIG. 26.

FIG. 27 shows a repairing procedure to be carried out by the wafer inspecting system. The position size and shape of the defect are estimated on the basis of infrared image information, visible image information and leakage current provided by the wafer inspecting system, the criticality of the defect is assessed on the basis of the amount of generated heat and short circuit resistance, and whether or not the defect is repairable is determined with reference to the classification models 456. The product is rejected if the defect is unrepairable. If the product has a repairable defect, the product is subjected to an automatic repairing process, in which a position to be irradiated with a laser beam, the length of the slit for the laser beam and the intensity of the laser beam are controlled by the machine parameter adjusting unit.

The classification models 456 for determining whether or not the defect is repairable, similarly to those for semiconductor wafer inspection, can be updated or new models can be registered by operating the terminal equipment. During the repairing operation, the result of classification of the defect is displayed for the operator. The repairing operation is continued if the defect is classified correctly, and a correct classification of the defect is entered by operating the terminal equipment and then the repairing operation is executed. Repair information is fed back to the classification models 456 to update the classification models 456.

The present invention is applicable also to processes of soldering, inspecting soldered parts and repairing soldered parts, processes of mounting electronic parts on a substrate, inspecting the electronic parts and repairing defective electronic parts, processes of manufacturing, inspecting and repairing thick-film and thin-film hybrid wafer, processes of manufacturing, inspecting and adjusting CRTs, such as CDT displays, and processes of electrical inspection of semiconductors.

The present invention has the following advantages.

(A) Since the inspecting standards of the automatic inspection unit can be automatically readjusted by the defect classifying and feature extracting unit 2 of FIG. 1 or can be semiautomatically readjusted through the feature data converting unit 3 of FIG. 1 under operator's supervision using the defect classification indicating unit 6 connected to the defect classifying and feature extracting unit 2, the inspecting standards can be readjusted to inspecting standards conforming to the process conditions without stopping the automatic inspection unit.

(B) Since the inspecting standards can be automatically readjusted by the defect classifying and feature extracting unit 2 of FIG. 1 or can be semiautomatically readjusted through the feature data comparing unit 3 of FIG. 1 under operator's supervision using the defect classification indicating unit 6 connected to the defect classifying and feature extracting unit 2, the inspecting reliability of the automatic inspection unit can be improved quickly.

(C) The advantage mentioned in (A) curtails time necessary for starting up the automatic inspection unit when products of one kind being inspected are changed for those of another kind.

(D) Since the advantage mentioned in (A) curtails time necessary for adjusting the automatic inspection unit, the number of products which are inspected on the basis of inappropriate inspecting standards can be reduced.

(E) Since the classification of defects by the defect classifying and feature extracting unit 2 of FIG. 1 enables the categories of defects to be know and thereby the manufacturing machines presumably causative of the defects can be determined. The manufacturing process can be stabilized quickly by adjusting the manufacturing machines taking into consideration the characteristics defects of the manufacturing machines through the operation of the feature-parameter conversion unit 4 of FIG. 1.

(F) The advantage mentioned in (B) enables correct instructions to be given to the repairing process, so that the incorrect repair of products can be prevented.

(G) The defect classifying and feature extracting unit 2 of FIG. 1 is adjusted while defects are removed by operating the defect classification input unit 10 connected to the repair unit 11 of FIG. 1 and, consequently, the inspecting standards by which the automatic inspection unit inspects products can be readjusted.

(H) The defect classification indicating unit 6 processes the information stored in the information storage unit 7 of FIG. 1 and indicates the processed information to enable the operator to grasp easily the relation between the causes of defects and the condition of the manufacturing process.

(I) Information given to the information storage unit 7 of FIG. 1 is transferred to the process control system 5 of FIG. 1 to enable the control of the condition of the entire manufacturing process.

(J) When the result of defect classification provided by the defect classifying and feature extracting unit 2 of the automatic inspection units installed respectively at different positions in the manufacturing process and the feature data of defects are compared and when the result of defect classification provided by the defect classifying and feature extracting unit 2 are similar to each other, a portion of the manufacturing process between the automatic inspection units connected to those defect classifying and feature extracting units 2 need not be monitored and hence either the automatic inspection unit on the upper side of the portion of the manufacturing process or the automatic inspection unit on the lower side of the portion of the manufacturing process may be omitted. Therefore, the automatic inspection units can be installed at optimum positions in the manufacturing process.

(K) Since the information attaching unit 14 of FIG. 1 attaches the result of inspection and the associated information to the inspected product, the manufacturing processes causative of the defects and the causal relation between defects detected by inspection at the final stage and those detected at the middle stage can be known by comparing the information attached to the product and the result of inspection in the following manufacturing processes or the result of final inspection.

What is claimed is:

1. A method of manufacturing a semiconductor device, comprising: extracting defects in a semiconductor device; classifying the defects according to an analogy of the defects with information about the extracted defects; extracting the feature data of the defects according to the result of defect classification; and feeding back the feature data of the extracted defect to an apparatus for manufacturing the semiconductor device.

2. A method of manufacturing a semiconductor device according to claim 1, wherein a pattern information about an image of the detected defect is used for representing an attribute of the defect.

3. A method of manufacturing a semiconductor device according to claim 1, wherein signal information about the detected defect is used for representing an attribute of the defect.

4. An apparatus for manufacturing a semiconductor device, comprising: an automatic inspection unit that extracts defects in a semiconductor device manufactured by a manufacturing machine, according to predetermined inspecting standards; a defect classifying and feature extracting unit (2) that receives information about the defects extracted by the automatic inspection unit, classifies the defects by category according to an analogy of the defects with information about the defects, provides the result of defect classification, and extracts the feature data of the defects on the basis of the result of defect classification; a control means that converts the feature data into control parameters for controlling the condition of the manufacturing machine, and controls the manufacturing machine according to the parameters.

5. An apparatus for manufacturing a semiconductor device according to claim 4, wherein the defect classifying and feature extracting unit (2) has a means capable of visually indicating the result of defect classification to the operator to enable the operator to confirm the result of the defect classification and the associated information, and to change the information or to add new information to the information.

6. An apparatus for manufacturing a semiconductor device according to claim 5 further comprising an information storage means for storing the information and information about each of the corresponding defects in a product.

7. An apparatus for manufacturing a semiconductor device according to claim 5, capable of extracting feature data of the defects from the information stored in the information storage means and the information about the corresponding defects in a product, and constructed so as to send the feature data to a feature data converting unit.

8. An apparatus for manufacturing a semiconductor device according to claim 4, wherein the defect classifying and feature extracting unit (2) has a means for visually indicating the result of defect classification to an operator to enable the operator confirm the result of defect classification and the associated information, and to change the information or to add new information to the information.

9. An apparatus for manufacturing a semiconductor device according to claim 4, wherein the information about the defect is image information about the detected defect and a region surrounding the detected defect.

10. An apparatus for manufacturing a semiconductor device according to claim 4, wherein the defect classifying and feature extracting unit sends the product inspected by the automatic inspection unit to a repairing unit according to the result of defect classification, and the product having the defect is subjected to a predetermined repairing process.

11. An apparatus for manufacturing a semiconductor device or the like according to claim 10, wherein the repairing operation of the repairing unit can be controlled by the operator, information about the correct result of defect classification can be given to the repairing unit when the result of defect classification provided by the defect classifying and feature extracting unit is incorrect, and the information about the correct result of defect classification can be fed back to the defect classifying and feature extracting unit.

* * * * *